United States Patent
Garland et al.

(10) Patent No.: US 11,446,303 B2
(45) Date of Patent: Sep. 20, 2022

(54) URIDINE PHOSPHORYLASE (UPASE) INHIBITORS FOR TREATMENT OF LIVER CONDITIONS

(71) Applicant: Tosk, Inc., Mountain View, CA (US)

(72) Inventors: William A. Garland, Mountain View, CA (US); Heshan Peiris, Mountain View, CA (US); Philip Liaw, Mountain View, CA (US); Brian D. Frenzel, Mountain View, CA (US)

(73) Assignee: Tosk, Inc., Mountain View, CA (US)

( * ) Notice: Subject to any disclaimer, the term of this patent is extended or adjusted under 35 U.S.C. 154(b) by 0 days.

(21) Appl. No.: 16/904,262

(22) Filed: Jun. 17, 2020

(65) Prior Publication Data

US 2020/0397790 A1    Dec. 24, 2020

Related U.S. Application Data

(60) Provisional application No. 62/864,695, filed on Jun. 21, 2019.

(51) Int. Cl.
*A61K 31/519* (2006.01)
*A61P 1/16* (2006.01)

(52) U.S. Cl.
CPC .............. *A61K 31/519* (2013.01); *A61P 1/16* (2018.01)

(58) Field of Classification Search
CPC ............................... A61K 31/519; A61P 1/16
USPC .................................................... 514/257, 50
See application file for complete search history.

(56) References Cited

U.S. PATENT DOCUMENTS

| | | | |
|---|---|---|---|
| 5,296,216 | A | 3/1994 | Turner |
| 5,736,531 | A | 4/1998 | von Borstel et al. |
| 5,968,914 | A | 10/1999 | von Borstel et al. |
| 6,232,298 | B1 | 5/2001 | von Borstel et al. |
| 6,344,447 | B2 | 2/2002 | von Borstel et al. |
| 6,992,072 | B2 | 1/2006 | Walker |
| 7,166,581 | B1 | 1/2007 | von Borstel et al. |
| 7,709,459 | B2 | 5/2010 | von Borstel et al. |
| 7,776,838 | B1 | 8/2010 | von Borstel et al. |

(Continued)

FOREIGN PATENT DOCUMENTS

| | | |
|---|---|---|
| JP | H06508846 A | 10/1994 |
| JP | H10511689 A | 11/1998 |

(Continued)

OTHER PUBLICATIONS

Le et al. "Uridine prevents fenofibrate-induced fatty liver," Plos One, 2014, vol. 9, issue 1, e87179, https://journals.plos.org/plosone/article/file?id=10.1371/journal.pone.0087179&type=printable (Year: 2014).*

(Continued)

*Primary Examiner* — Shengjun Wang
(74) *Attorney, Agent, or Firm* — Bret E. Field; Bozicevic, Field & Francis LLP

(57) ABSTRACT

Methods of treating a subject for a liver condition, e.g., NAFLD, NASH, and/or DILI, are provided. Aspects of the methods include administering to the subject an effective amount of a UPase inhibitor, optionally in combination with a uridine active agent (e.g., uridine (UR), a UR pro-drug or a UR mimetic), such as supplemental uridine, to treat the subject for the liver condition. Also provided are compositions for use in practicing the subject methods.

18 Claims, 4 Drawing Sheets

(56) References Cited

U.S. PATENT DOCUMENTS

| | | | |
|---|---|---|---|
| 7,998,967 | B2 | 8/2011 | Garland et al. |
| 8,853,227 | B2 | 10/2014 | Garland et al. |
| 9,700,547 | B2 | 7/2017 | Basso et al. |
| 2004/0029823 | A1 | 2/2004 | McKay et al. |
| 2005/0090551 | A1 | 4/2005 | Campbell |
| 2006/0040890 | A1 | 2/2006 | Martin et al. |
| 2008/0269185 | A1 | 10/2008 | Rothstein et al. |
| 2011/0319419 | A1 | 12/2011 | Garland et al. |
| 2012/0029071 | A1 | 2/2012 | Biswal et al. |
| 2012/0189629 | A1 | 7/2012 | Smith |
| 2012/0294869 | A1 | 11/2012 | Pizzomo et al. |
| 2015/0072945 | A1 | 3/2015 | Garland et al. |

FOREIGN PATENT DOCUMENTS

| | | |
|---|---|---|
| KR | 101195019 B1 | 10/2012 |
| WO | WO9301202 A1 | 1/1993 |
| WO | WO9426761 A1 | 11/1994 |
| WO | WO03099297 A1 | 12/2003 |
| WO | 2004024095 A2 | 3/2004 |
| WO | WO2008083465 A1 | 7/2008 |

OTHER PUBLICATIONS

Cicko et al. Uridine supplementation exerts anti-inflammatory and anti-fibrotic effect in an animal model of pulmonary fibrosis, Respiratory Research, 2015, 16:105 (Year: 2015).*

Labbe et al. "Drug induced liver injury through mitochondrial dysfunction: mechanism and detection during preclin" Fundamental & Clinical Pharmacology, 2008, vol. 22, Issue 4, pp. 335-353. (Year: 2008).*

Ashour et al., 5-(m-Benzyloxybenzyl)barbituric acid acyclonucleoside, a uridine phosphorylase inhibitor, and 2',3',5'-tri-O-acetyluridine, a prodrug of uridine, as modulators of plasma uridine concentration. Implications for chemotherapy, Biochem Pharmacol (1996), 51(12):1601-1611.

Ashour et al., Effect of 5-(phenylselenenyl)acyclouridine, an inhibitor of uridine phosphorylase, on plasma concentration of uridine released from 2',3',5'-tri-O-acetyluridine, a prodrug of uridine: relevance to uridine rescue in chemotherapy, Cancer Chemother Pharmacol (2000), 46(3):235-240.

Ashour et al., Modulation of 5-fluorouracil host toxicity by 5-(benzyloxybenzyl)barbituric acid acyclonucleoside, a uridine phosphorylase inhibitor, and 2',3',5'-tri-O-acetyluridine, a prodrug of uridine, Biochem Pharmacol (2000), 60(3):427-431.

Brunetti et al., 5-Fluorouracil enhances azidothymidine cytotoxicity: in vitro, in vivo, and biochemical studies, Cancer Res (1990), 50(13):4026-4031.

Christensen et al., Effect of hydration on methotrexate plasma concentrations in children with acute lymphocytic leukemia, J Clin Oncology (1988), 6(5):797-801.

Darnowski et al., Fluorouracil plus azidothymidine cytotoxicity in vitro: Relationship to cellular thymidine kinase activity, Proc of American Assoc for Cancer Research (1990), 31:398.

Darnowski et al., Resistance to Azido-Thymidine Cytotoxicity in the Human Colon Tumor Cell Line HCT15 is Associated with Enhanced Removal of AZT from Cellular DNA, Proc of American Assoc for Cancer Research (1991), 32:358.

Drabikowska et al., Inhibitor properties of some 5-substituted uracil acyclonucleosides, and 2,2'-anhydrouridines versus uridine phosphorylase from E. coli and mammalian sources, Biochem Pharmacol (1987), 36(23):4125-4128.

Ettmayer et al., Lessons learned from marketed and investigational prodrugs, Medicinal Chemistry (2004), 47(10):2393-2404.

Howell et al., Cytokinetic comparison of thymidine and leucovorin rescue of marrow in humans after exposure to high-dose methotrexate, Cancer Res (1979), 39(4):1315-1320.

Howell et al., Thymidine Rescue of High-Dose Methotrexate in Humans, Cancer Res (1978), 38(2): 325-330.

Iigo et al., Differential effects of 2,2'-anhydro-5-ethyluridine, a uridine phosphorylase inhibitor, on the antitumor activity of 5-fluorouridine and 5-fluoro-2'-deoxyuridine, Biochem Pharmacol (1990), 39(7):1247-1253.

Martin et al., High-dose 5-fluorouracil with delayed uridine "rescue" in mice, Cancer Res (1982), 42(10):3964-3970.

Martin et al., Use of oral uridine as a substitute for parenteral uridine rescue of 5-fluorouracil therapy, with and without the uridine phosphorylase inhibitor 5-benzylacyclouridine, Cancer Chemother Pharmacol (1989), 24(1):9-14.

Mazokopakis et al., Wild chamomile (*Matricaria recutita* L.) mouthwashes in methotrexate-induced oral mucositis, Phytomedicine (2005), 12(1-2):25-27.

Morissette et al., High-throughput crystallization: polypmorphs, salts, co-crystals and solvates of phramaceutical solids, Adv Drug Deliv Rev (2004), 56(3):275-300.

Newman et al., Increased Sensitivity to Azidothymidine in a Subline of CCRF-CEM Human Leukemia Cells Resistant to Methotrexate, Proceedings of the American Assoc. for Cancer Research (1991), 32:413.

Pizzorno et al., Phase I clinical and pharmacological studies of benzylacyclouridine, a uridine phosphorylase inhibitor, Clin Cancer Res (1998), 4(5):1165-1175.

Scanlon et al.,Overexpression of DNA replication and repair enzymes in cisplatin-resistant human colon carcinoma HCT8 cells and circumvention by azidothymidine, Cancer Commun (1989), 1(4):269-275.

Semon et al., Potentiation of the Antitumor Activity of Methotrexate by Concurrent Infusion of Thymidine, Cancer Res (1978), 38:2905-2911.

Stella, Prodrugs as therapeutics, Expert Opinion on Therapeutic Patents (2004), 14,(3):277-280.

Sterba et al., High-dose methotrexate and/or leucovorin rescue for the treatment of children with lymphoblastic malignancies: do we really know why, when and how?, Neoplasma (2005), 52 6):456-463.

Tattersall et al., The reversal of methotrexate toxicity by thymidine with maintenance of antitumour effects, Nature (1975), 253 (5488):198-200.

Testa, Prodrug research: futile or fertile?, Biochemical Pharmacology (2004), 68(11):2097-2106.

Tosi et al., Azidothymidine-induced cytotoxicity and incorporation into DNA in the human colon tumor cell line HCT-8 is enhanced by methotrexate in vitro and in vivo, Cancer Res (1992), 52(15):4069-4073.

Veres et al., 5-Substituted-2,2'-anhydrouridines, potent inhibitors of uridine phosphorylase, Biochem Pharmacol (1985), 34(10):1737-1740.

Veres et al., Inhibition of uridine phosphorylase by pyrimidine nucleoside analogs and consideration of substrate binding to the enzyme based on solution conformation as seen by NMR spectroscopy, Eur J Biochem (1988), 178(1):173-181.

Vippagunta et al. Crystalline solids, Adv Drug Deliv Rev (2001), 48(1):3-26.

Weber et al., Azidothymidine inhibition of thymidine kinase and synergistic cytotoxicity with methotrexate and 5-fluorouracil in rat hepatoma and human colon cancer cells, Cancer Commun (1990), 2(4):129-133.

Weber et al., AZT: a biochemical response modifier of methotrexate and 5-fluorouracil cytotoxicity in human ovarian and pancreatic carcinoma cells, Cancer Commun (1991), 3(4):127-132.

Weber et al., Regulation of de novo and salvage pathways in chemotherapy, Adv Enzyme Regul (1991), 31:45-67.

Wolff, Burger's Medicinal Chemistry and Drug Discovery, 5th edition (1994), vol. 1, pp. 975-977.

Veres et al., "The effect of the 3'-OH group on the conformation and binding ability of anhydropyrimidine nucleosides to uridine phosphorylase", Archives of Biochemistry and Biophysics, Apr. 1991, vol. 286, No. 1, pp. 1-5, abstract only.

Grancharov et al., "Inhibition of uridine phosphorylase by some pyrimidine derivatives", Biochemical Pharmacology, 1991, vol. 41, p. 1769-1772, abstract only.

(56) References Cited

OTHER PUBLICATIONS

Iigo et al., "In vivo Antitumor Effects of Fluoropyrimidines on Colon Adenocarcinoma 38 and Enhancement by Leucovorin", Jpn. J. Cancer Res., 1992, vol. 83, p. 392-396.
Da Silva et al., Therapeutic effect of uridine phosphorylase 1 (UPP1) inhibitor on liver fibrosis in vitro and in vivo, European Journal of Pharmacology, Jan. 2021, vol. 890, No. 173670, p. 1-11.
Leyva et al., Phase I and Pharmacokinetic Studies of High-Dose Uridine Intended for Rescue from 5-Fluorouracil Toxicity, Cancer Research, Dec. 1984, vol. 44, p. 5928-5933.
Maria et al., Radiation-Induced Oral Mucositis, Frontiers in Oncology, May 2017, vol. 7, Art. 89, p. 1-23.
Renck et al., Human uridine phosphorylase-1 inhibitors: a new approach to ameliorate 5-fluorouracil-induced intestinal mucositis, Invest New Drugs, Jul. 2014, vol. 32, p. 1301-1307.
Al Safarjalani et al., 5-(Phenylthio)acyclouridine: a powerful enhancer of oral uridine bioavailability: relevance to chemotherapy with 5-fluorouracil and other uridine rescue regiments, Cancer Chemother Pharmacol, Feb. 2005, vol. 55, p. 541-551.
PubChem CID 73805817, May 29, 2014, Retrieved from the Internet on May 4, 2022, URL: https://pubchem.ncbi.nlm.nih.gov/compound/73805817, 8 pages.
Tang et al., Inhibition of Autotaxin with GLPG1690 Increases the Efficacy of Radiotherapy and Chemotherapy in a Mouse Model of Breast Cancer, Molecular Cancer Therapeutics, Sep. 23, 2019, pp. 1-13.

\* cited by examiner

URIDINE PHOSPHORYLASE (UPASE) INHIBITORS FOR TREATMENT OF LIVER CONDITIONS

CROSS-REFERENCE TO RELATED APPLICATIONS

Pursuant to 35 U.S.C. § 119(e), this application claims priority to the filing date of U.S. Provisional Patent Application Ser. No. 62/864,695 filed Jun. 21, 2019; the disclosure of which application is herein incorporated by reference.

INTRODUCTION

The prevalence of nonalcoholic fatty liver disease (NAFLD) and nonalcoholic steatohepatitis (NASH), a more severe form of NAFLD, is increasing rapidly worldwide.[1] NAFLD features hepatic fat accumulation (steatosis), occasional fibrosis, and hepatocyte ballooning as the result of accumulation of fat (triglyceride) droplets with no other cause of secondary hepatic fat accumulation (e.g., alcohol, infections, medications, etc.).[2] In addition to hepatocyte ballooning and fat accumulation, like found in NALFD, NASH also features lobular inflammation, fibrosis, and hepatocyte degeneration. For NASH, the fibrosis is typically followed by cirrhosis and end-stage liver disease, which is typically fatal without a liver transplant.[3] In addition to end-stage liver disease, individuals with NASH often also develop liver cancer (hepatocellular cancer, HCC) as the result of the condition.[4,5]

[1] Jennings J, Faselis C, Yao M D. NAFLD-NASH: An Under-Recognized Epidemic. Curr Vasc Pharmacol. 018; 16:209-213.
[2] Koch L K, Yeh M M. Nonalcoholic fatty liver disease (NAFLD): Diagnosis, pitfalls, and staging. Ann Diagn Pathol. 2018; 37:83-90.
[3] Alkhouri N, Lawitz E, Noureddin M. Looking Into the Crystal Ball: Predicting the Future Challenges of Fibrotic NASH Treatment. Hepatol Commun. 2019; 3:605-613.
[4] Anstee Q M, Reeves H L, Kotsiliti E, Govaere O, Heikenwalder M. From NASH to HCC: current concepts and future challenges. Nat Rev Gastroenterol Hepatol. 2019 Apr. 26.
[5] Dhanasekaran R, Felsher D W. A Tale of Two Complications of Obesity: Nonalcoholic steatohepatitis (NASH) and Hepatocellular carcinoma (HCC). Hepatology. 2019 Apr. 8.

The increased prevalence of both NALFD and NASH mirrors the societal increase in obesity and type 2 diabetes (T2D), and reflects the hepatic manifestation of the resulting altered metabolic state.[6] The exposure of hepatocytes to high concentrations of lipids and carbohydrates, termed lipotoxicity and glucotoxicity, respectively, underlie much of the hepatocellular injury observed in NAFLD/NASH.[7] Metabolic syndrome, defined as a constellation of obesity, insulin resistance, hyperglycemia, dyslipidemia and hypertension, is the major risk factor predisposing individuals to NAFLD and NASH.[8] Approximately 30% of North Americans suffer from NALFD and 4% from NASH.[9] Genetic, demographic, and ethnic factors may also play a role in the pathogenesis of NAFLD,[10] for example:
- NAFLD has been linked with various genetic variants, including PNPLA-3, TM6SF2, and FDFT1.
- NAFLD is more common in older age groups and in men.
- Hispanics have the highest prevalence of NAFLD in the US, followed by Caucasians and then African Americans.

[6] Esler W P, Bence K K. Metabolic Targets in Nonalcoholic Fatty Liver Disease. Cell Mol Gastroenterol Hepatol. 2019 Apr. 18.
[7] Mota M, Banini B A, Cazanave S C, Sanyal A J, Molecular mechanisms of lipotoxicity and glucotoxicity in nonalcoholic fatty liver disease. Metabolism. 2016, 65:1049-61.
[8] Aguilar-Salinas Calif., Viveros-Ruiz T. Recent advances in managing/understanding the metabolic syndrome. F1000Res. 2019 Apr. 3; 8.
[9] Garber K. The new liver epidemic. Nat Biotechnol. 2019; 37:209-214.
[10] Iqbal U, Perumpail B J, Akhtar D, Kim D, Ahmed A. The Epidemiology, Risk Profiling and Diagnostic Challenges of Nonalcoholic Fatty Liver Disease. Medicines (Basel). 2019; 6(1).

There are no US Food and Drug Administration (FDA) approved medications to treat patients with NASH. Current recommended actions to treat the disease include weight loss and dietary modifications, e.g., lowering consumption of fats and glucose.[11] The only known "cure" for late-stage NASH and/or HCC is a liver transplant. In this regard, NASH is set to soon overtake hepatitis as the single leading factor leading to liver transplantation.[9]

[11] Huang M A, Greenson J K, Chao C, Anderson L, Peterman D, Jacobson J, Emick D, Lok A S, Conjeevaram H S. One-year intense nutritional counseling results in histological improvement in patients with non-alcoholic steatohepatitis: a pilot study. Am J Gastroenterol. 2005; 100:1072-81.

Lipid Droplets (LD), also referred to as lipid bodies, oil bodies, or adiposomes are dynamic organelles that store neutral lipids during periods of energy excess, and serve as an energy reservoir during deprivation.[12] Many prevalent metabolic diseases, such as metabolic syndrome and obesity, often result in elevated lipids and increased LDs in the liver, also called hepatic steatosis/NAFLD. LD, and particularly proteins associated with LD, are strongly associated with the pathophysiology of fatty liver disease.[13] Under normal physiologic conditions, hepatic LDs are small and present in limited numbers. More substantial LD formation is associated with hepatotoxicity post administration to animals or man of drugs such as tamoxifen (TAM),[14,15,16,17] cyclosporin,[18] valproic acid,[19,20] tetracyclines,[21] clofibrate,[22] olanzapine,[23] and statins such as simavastin,[24] etc. LDs appear to have a close relationship with mitochondria, including physical contact and protein shuttling.[25] LDs also appear to have a similar intimate relationship with the cell nucleus.[26] The content of the LD appears to determine its potential for toxicity-LDs containing unsaturated fatty acids like arachidonic acid, the precursor to many inflammatory mediators,[27] are more toxic than LDs containing saturated fatty acids.[28] LDs are coated with proteins from the perilipin family, some of which are involved in the regulation of lipid metabolism.[29]

[12] Meyers A1, Weiskittel TM1, Dalhaimer P2,3. Lipid Droplets: Formation to Breakdown. Lipids. 2017: May 20 [Epub ahead of print]
[13] Okumura T, Role of lipid droplet proteins in liver steatosis. J Physiol Biochem. 2011; 67: 629-36.
[14] Nishino M, Hayakawa K, Nakamura Y, Morimoto T, Mukaihara S. Effects of tamoxifen on hepatic fat content and the development of hepatic steatosis in patients with breast cancer: high frequency of involvement and rapid reversal after completion of tamoxifen therapy. AJR Am J Roentgenol 2003; 180: 129-134.
[15] Ogawa Y, Murata Y, Nishioka A, Inomata T, Yoshida S, Tamoxifen-induced fatty liver in patients with breast cancer. Lancet 1998; 351(9104):725.
[16] Nguyen M C, Stewart R B, Banerji M A, Gordon D H, Kral J G. Relationships between tamoxifen use, liver fat and body fat distribution in women with breast cancer. Int J Obes Relat Metab Disord 2001; 25(2): 296-298.
[17] Lüllmann H, Lüllmann-Rauch R. Tamoxifen-induced generalized lipidosis in rats subchronically treated with high doses. Toxicol. Appl. Pharmacol. 1981; 61: 138-146.
[18] Wolf A, Trendelenburg C F, Diez-Fernandez C, Prieto P, Houy S, Trommer W E, Cordier A. Cyclosporine A-induced oxidative stress in rat hepatocytes. J. Pharmacol. Exp. Ther. 1996; 280: 1328-1334.
[19] Tong V, Teng X W, Chang T K, Abbott F S. Valproic acid I: time course of lipid peroxidation biomarkers, liver toxicity, and valproic acid metabolite levels in rats. Toxicol. Sci. 2005; 86: 427-435.
[20] Tong V, Teng X W, Chang T K, Abbott F S. 2005b. Valproic acid II: effects on oxidative stress, mitochondrial membrane potential, and cytotoxicity in glutathione-depleted rat hepatocytes. Toxicol. Sci. 2005; 86: 436-443.
[21] Amacher D E, Martin B A. Tetracycline-induced steatosis in primary canine hepatocyte cultures. Fundam. Appl. Toxicol. 1997; 40: 256-263.
[22] Meijer J, Afzelius B A. Effects of clofibrate treatment and of starvation on peroxisomes, mitochondria, and lipid droplets in mouse hepatocytes: a morphometric study. J Ultrastruct Mol Struct Res. 1989; 102: 87-94.

[23] Nimura S, Yamaguchi T, Ueda K, Kadokura K, Aiuchi T, Kato R, Obama T, Itabe H. Olanzapine promotes the accumulation of lipid droplets and the expression of multiple perilipins in human adipocytes. Biochem Biophys Res Commun. 2015; 467: 906-12.

[24] Gbelcová H, Svéda M, Laubertová L, Varga I, Vítek L, Kolář M, Strnad H, Zelenka J, Böhmer D, Ruml T. The effect of simvastatin on lipid droplets accumulation in human embryonic kidney cells and pancreatic cancer cells. Lipids Health Dis. 2013; 12:126.

[25] Bischof J, Salzmann M, Streubel M K, Hasek J, Geltinger F, Duschl J, Bresgen N, Briza P, Haskova D, Lejskova R, Sopjani M, Richter K, Rinnerthaler M. Clearing the outer mitochondrial membrane from harmful proteins via lipid droplets. Cell Death Discov. 2017; 3:17016.

[26] Welte M A. Expanding roles for lipid droplets. Curr Biol. 2015; 25: R470-81.

[27] Martin S A, Brash A R, Murphy R C. The discovery and early structural studies of arachidonic acid. J Lipid Res. 2016; 57: 1126-32.

[28] Czamara K, Majzner K, Selmi A, Baranska M, Ozaki Y, Kaczor A. Unsaturated lipid bodies as a hallmark of inflammation studied by Raman 2D and 3D microscopy. Sci Rep. 2017; January 18; 7:40889.

[29] Itabe H, Yamaguchi T, Nimura S, Sasabe N. Perilipins: a diversity of intracellular lipid droplet proteins. Lipids Health Dis. 2017; 16: 83.

A major liver-related public health problem is drug induced liver disease (DILI). affecting individuals consuming pharmaceutical or nutraceuticals. DILI has been linked to over 1000 drugs.[30] Although complete recovery is expected for patients experiencing less serious DILI, the associated symptoms (e.g., fatigue, itching, nausea) can be debilitating and recovery can be prolonged, with about 20% of patients having biochemical evidence of continuing liver injury 6 months after diagnosis.[31] Cirrhosis and long-term liver-related morbidity and mortality occur in approximately 3% of cases.[32] Currently no tests are available to physicians to confidently diagnosis DILI.[33] A DILI, or even the suspicion of a DILI, may lead to use of an alternate treatment, resulting in exposure to new adverse drug event risks and possible suboptimal treatment of the underlying disease. DILIs also are a common cause for termination of clinical drug development programs.[34] DILI results in a range of pathologies. These pathologies range from elevation of serum transaminase levels, detected on routine, biochemical laboratory testing, that resolves after removal of the offending chemical agent to acute liver failure, defined as de novo, sudden, and life-threatening liver dysfunction that leads to coagulopathy and hepatic encephalopathy within 26 weeks of the onset of illness.[35] Acute liver failure is a devastating disease since it primarily affects young, healthy individuals and leads to death in approximately 30% of patients receiving aggressive therapy, including liver transplant.

[30] Iorga A, Dara L, Kaplowitz N. Drug-Induced Liver Injury: Cascade of Events Leading to Cell Death, Apoptosis or Necrosis. Int J Mol Sci. 2017; 18(5). E1018.

[31] Fontana, R. J. et al. Idiosyncratic drug-induced liver injury is associated with substantial morbidity and mortality within 6 months from onset. Gastroenterology. 2014; 147, 96-108.

[32] Saithanyamurthi H, Faust A J. Drug-Induced Liver Disease: Clinical Course. Clin Liver Dis. 2017; 21: 21-34.

[33] Mosedale M, Watkins P B. Drug-induced liver injury: Advances in mechanistic understanding that will inform risk management. Clin Pharmacol Ther. 2017; 101: 469-480.

[34] Watkins P B, Drug safety sciences and the bottleneck in drug development. Clin Pharmacol Ther 2011; 89: 788-790.

[35] Fisher K, Vuppalanchi R, Saxena R. Drug-Induced Liver Injury. Arch Pathol Lab Med. 2015; 139: 876-87

There are two types of DILI, "intrinsic" and "idiosyncratic."

Drugs that induce liver injury in a predictable, dose-dependent manner in both preclinical models and humans are said to cause intrinsic DILI. Acetaminophen is the most common cause of intrinsic DILI in the US. Few other drugs on the market cause life-threatening, intrinsic DILI because this liability is generally identified during preclinical or early clinical studies. Such drugs are often abandoned from further development, used at doses below that providing optimum efficacy but anticipated to not cause liver injury, or administered in controlled or desperate situations, eg, chemotherapy. Except for N-acetyl cysteine to treat acetaminophen overdose, there is no treatment available for intrinsic DILIs, and N-acetyl cysteine is useful in only limited clinical circumstances.

Idiosyncratic DILI is the most problematic form of DILI. It occurs infrequently among treated patients, often after several months of treatment with the offending drug. Idiosyncratic DILI for a new drug is often only discovered when the drug enters general use. Idiosyncratic DILI with latency likely reflects an immune attack on the liver. Consistent with this view, idiosyncratic liver injury will recur promptly after complete recovery if the DILI patient is re-challenged with the offending drug. The prolonged latency can be attributed to the time required for antigen-specific lymphocytes to be activated and proliferate to enough numbers to mediate the DILI. The likely first step in initiating idiosyncratic DILI is formation of a hepatocyte stress inducing neoantigen.

Both intrinsic and idiosyncratic liver damage appears to proceed through similar processes. Proposed mechanisms include mitochondrial dysfunction, oxidative stress, and alterations in bile acid homeostasis. Mitochondria produce ATP that is required to maintain all vital cellular functions. DILI-causing drugs can inhibit mitochondrial function, resulting in reduced levels of ATP, a decline in cell function, and eventually cell death.[36] Oxidative stress is the result of ROS that are a byproduct of normal metabolism and have roles in cell signaling and homeostasis. However, some DILI-causing drugs can increase ROS accumulation through a variety of mechanisms.[37] When the processes that exist to regulate cellular levels of ROS are exceeded, oxidative stress can result in damage to key cellular components and eventually cell death. Finally, a major function of the liver is the transport of bile salts from blood into bile. DILI-causing drugs can disrupt this process in many ways, most importantly through reducing hepatic bile acid efflux by inhibition of the bile salt export protein.[38] This results in the intracellular accumulation of toxic bile acids which can lead to hepatocyte death. In summary, DILI appears in two different variants, intrinsic or idiosyncratic, with similar pathology and pathogenesis, but likely with multiple mechanisms of initiation and promotion.

[36] Will, Y. & Dykens, J. Mitochondrial toxicity assessment in industry—a decade of technology development and insight, Expert Opin Drug Metab Toxicol. 2014; 10:1061-1067.

[37] Gomez-Lechon, M J, Tolosa, L, Donato, M T. Metabolic activation and drug-induced liver injury: in vitro approaches for the safety risk assessment of new drugs. J Appl Toxicol. 2016; 36: 752-768.

[38] Morgan R E, van Staden C J, Chen Y, Kalyanaraman N, Kalanzi J, Dunn R T 2nd, Afshari C A, Hamadeh H K. A multifactorial approach to hepatobiliary transporter assessment enables improved therapeutic compound development. Toxicol Sci. 2013; 136: 216-241.

The link between NAFLD/NASH and DILI in a still not completely understood.[39,40,41,42,43,44] However, (1) DILI is a risk factor in NAFLD/NASH patients for many drugs, (2) DILI presents as lesions that resemble those of NAFLD/NASH, (3) the pathophysiology of DILI and NASH overlap, (4) certain drugs induce hepatic steatosis (DIS) and/or steatohepatitis (DISH) by triggering pathological events similar to those occurring in the development and progression NAFLD/NASH, (5) DILI influences the development or accelerates progression of NAFLD/NASH, and (6)

NAFLD/NASH affects the susceptibility to, and outcome of, DILI.

[39] Massart J, Begriche K, Moreau C, Fromenty B. Role of nonalcoholic fatty liver disease as risk factor for drug-induced hepatotoxicity. J Clin Transl Res. 2017; 3 (Suppl 1):212-232

[40] Ortega-Alonso A, Andrade R J. Chronic liver injury induced by drugs and toxins. J Dig Dis. 2018; 19:514-521.

[41] Spinnenhirn V, Demgenski J, Brunner T. Death Receptor Interactions With the Mitochondrial Cell Death Pathway During Immune Cell-, Drug- and Toxin-Induced Liver Damage. Front Cell Dev Biol. 2019; 7:72.

[42] Pavlik L, Regev A, Ardayfio P A, Chalasani N P. Drug-Induced Steatosis and Steatohepatitis: The Search for Novel Serum Biomarkers Among Potential Biomarkers for Non-Alcoholic Fatty Liver Disease and Non-Alcoholic Steatohepatitis. Drug Saf. 2019 June; 42:701-711.

[43] Regev A, Palmer M, Avigan M I, Dimick-Santos L, Treem W R, Marcinak J F, Seekins D, Krishna G, Anania F A, Freston J W, Lewis J H, Sanyal A J, Chalasani N. Consensus: guidelines: best practices for detection, assessment and management of suspected acute drug-induced liver injury during clinical trials in patients with nonalcoholic steatohepatitis. Aliment Pharmacol Ther. 2019; 49:702-713.

[44] Massart J, Begriche K, Moreau C, Fromenty B. Role of nonalcoholic fatty liver disease as risk factor for drug-induced hepatotoxicity. J Clin Transl Res. 2017; 3(Suppl 1):212-232.

Harmful effects from DILI not only can mimic the physiologic insults that trigger the development and/or progression of NAFLD in the normal liver but also aggravate similar alterations pre-existing in a fatty liver. Relative to NAFLD/NASH, DILI:

Exacerbates predisposing factors (e.g., obesity, diabetes)

Enhances steatotic factors (eg, exacerbates lipid hepatic synthesis/uptake)

Increases Inflammatory factors (eg, accumulation of lipotoxic fatty acids and oxidative stress)

Activates fibrogenic factors (eg, enhanced collagen deposition)

Alters drug-metabolic systems that occur in the NAFLD context Based on the above, an agent that mitigates NAFLD/NASH likely would also act to treat DILI and vice-versa.

NAFLD/NASH has become a significant, potentially lethal, health epidemic in countries suffering increased prevalence of obesity and the associated metabolic disorders for which there are no approved treatments. DILI, another serious hepatic condition appears to mimic the pathophysiology of NAFLD/NASH.

SUMMARY

Methods of treating a subject for a liver condition, e.g., NAFLD, NASH, and/or DILI, are provided. Aspects of the methods include administering to the subject an effective amount of a UPase inhibitor, optionally in combination with a uridine active agent (e.g., uridine (UR), a UR pro-drug or a UR mimetic), such as supplemental uridine, to treat the subject for the liver condition. Also provided are compositions for use in practicing the subject methods.

DEFINITIONS

Figure 1:
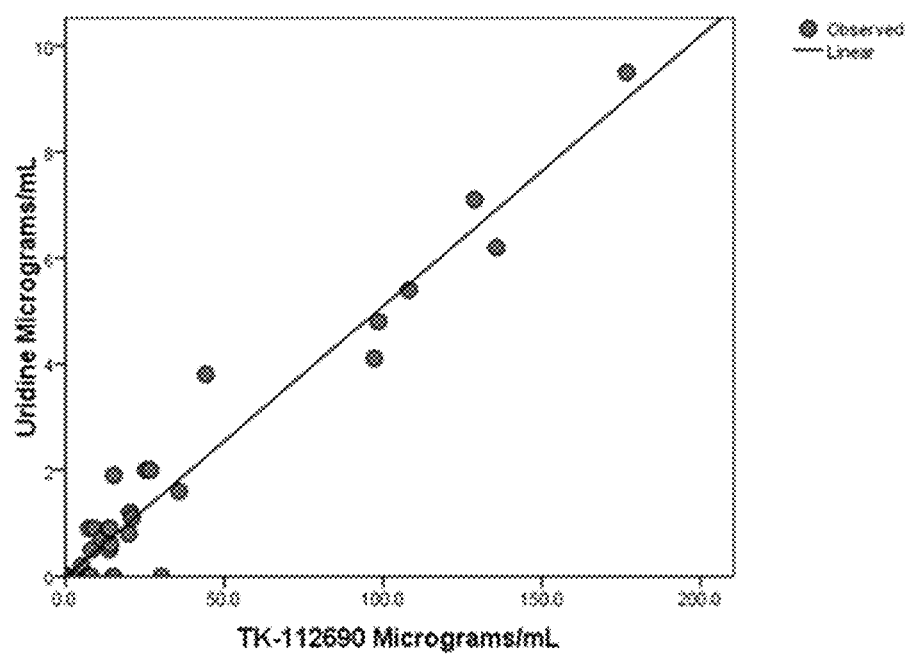
FIG. 1 provides a regression analysis of plasma UR concentration versus plasma Compound 1 concentrations determined following continuous infusion of various amounts of Compound 1 (TK-112690) to mice. R2 for the line is 0.95, and the slope and intercept values for the line are 0.010 and 0.051, respectively. Compound 1 is seen to elevate plasma UR in a linear fashion.

The following terms have the following meanings unless otherwise indicated when describing the compounds, pharmaceutical compositions containing such compounds, methods of using such compounds and compositions, and the description of the biology and pharmacology for use of the compounds, It should also be understood that any of the moieties defined forth below may be substituted with a variety of substituents, and that the respective definitions are intended to include such substituted moieties within their scope.

"Acyl" refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)— cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein. Structures for a few exemplary alkyl groups are provided in Table 1 below.

TABLE 1

Structure of exemplary alkyl groups

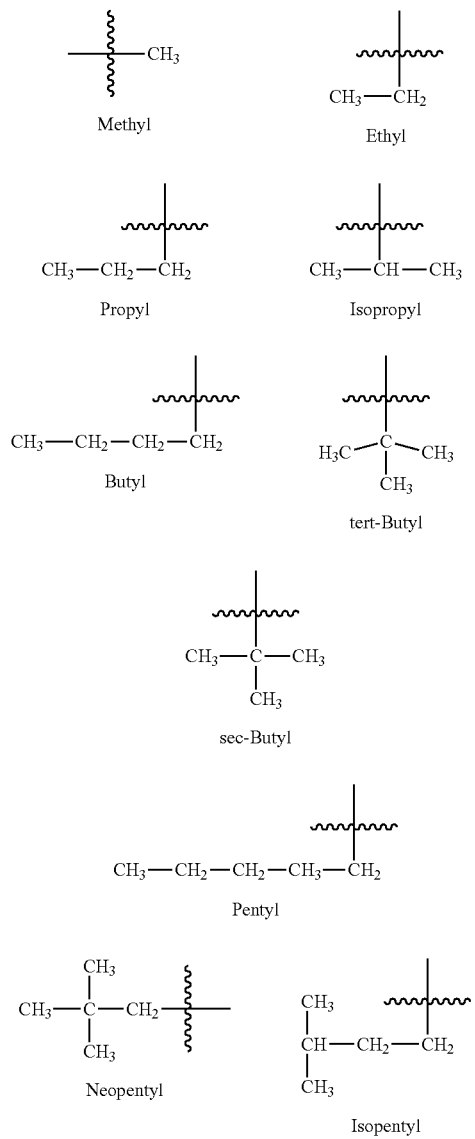

TABLE 1-continued

Structure of exemplary alkyl groups

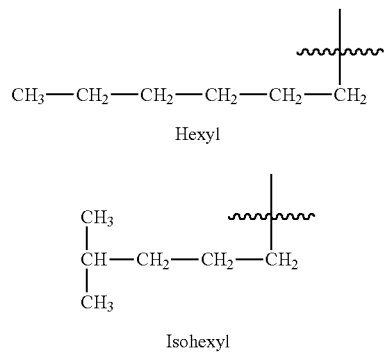

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—$CH_2$—), ethylene (—$CH_2CH_2$—), the propylene isomers (eg, —$CH_2CH_2CH_2$— and —$CH(CH_3)$ $CH_2$—) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2$C≡CH), and the like.

"Amino" refers to the radical —$NH_2$.

"Amino acid" refers to any of the naturally occurring amino acids (eg Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (eg, as in glycine), alkyl (eg, as in alanine, valine, leucine, isoleucine, proline), substituted alkyl (eg, as in threonine, serine, methionine, cysteine, aspartic acid, asparagine, glutamic acid, glutamine, arginine, and lysine), alkaryl (eg, as in phenylalanine and tryptophan), substituted arylalkyl (eg, as in tyrosine), and heteroarylalkyl (eg, as in histidine).

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like."

"ARMD" refers to an eye disease age related macular degeneration.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms. The structures of a few exemplary aryl groups are provided in Table 2.

TABLE 2

Examples of aryl groups

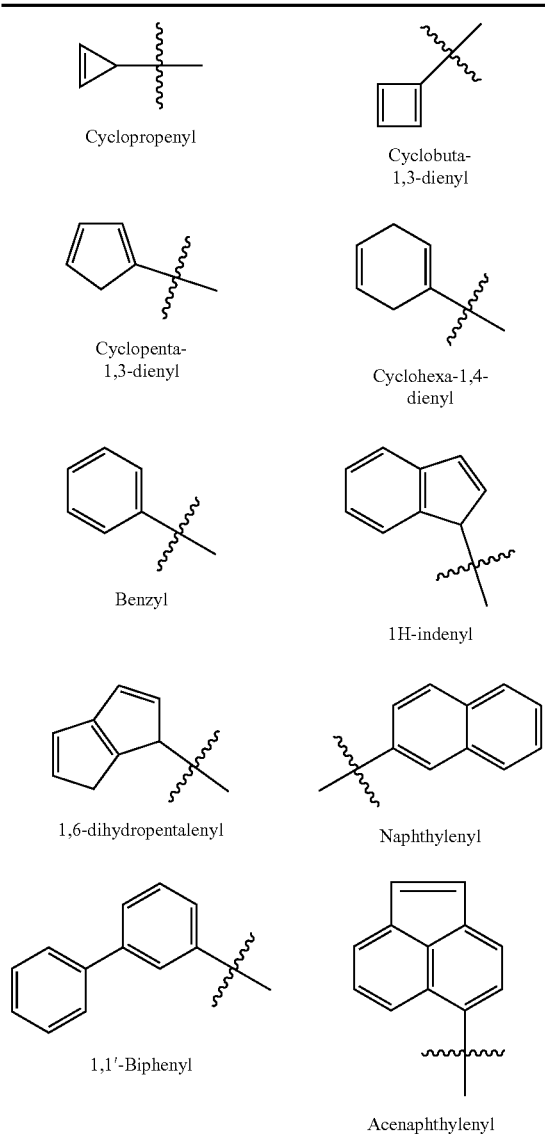

TABLE 2-continued

Examples of aryl groups

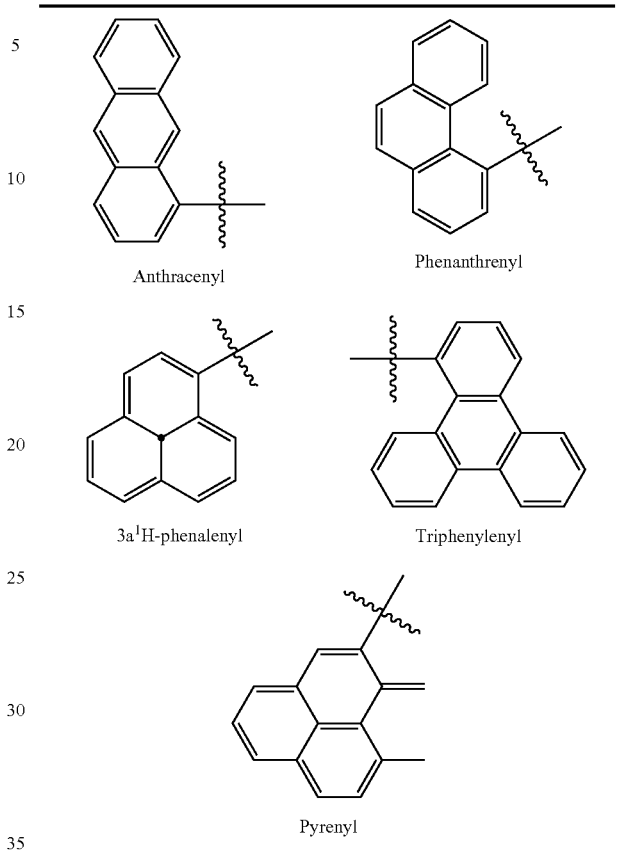

"Aryloxy" refers to —O-aryl groups wherein "aryl" is as defined herein.

"Autoimmune disease" or "autoimmune condition" refers an illness that occurs when the body tissues are attacked by its own immune system. Examples of autoimmune disease or conditions include multiple sclerosis, ankylosing spondylitis, Crohn's disease, arthritis, psoriasis, Behçet's disease and psoriatic arthritis.

Azido" refers to the radical —$N_3$.

"Carbohydrate" means a mono-, di-, tri-, or polysaccharide, wherein the polysaccharide can have a molecular weight of up to about 20,000, for example, hydroxypropylmethylcellulose or chitosan. "Carbohydrate" also encompasses oxidized, reduced or substituted saccharide monoradical covalently attached to the anhydropyrimidine (eg, anhydrothymidine or anhydrouridine), or derivative thereof any atom of the saccharide moiety, eg, via the aglycone carbon atom. The "mono-, di-, tri-, or polysaccharide" can also include amino-containing saccharide groups. Representative "carbohydrate" include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose-, 2-O-(3-desmethyl-α-L-vancosaminyl)-β-D-glucopyranose, sucrose, lactose, or maltose;

derivatives such as acetals, amines, acylated, sulfated and phosphorylated sugars; oligosaccharides having from 2 to 10 saccharide units. The saccharides can be either in their open, r pyranose or furanose forms.

"Carboxyl" refers to the radical —C(O)OH.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"DILI" refers drug-induced liver injury

"DIS" refers drug-induced hepatic steatosis

"DISH" refers to drug-induced steatohepatitis.

"DR" refers to an eye condition, diabetic retinopathy.

"FU" refers to 5-fluorouracil,

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl. The structures of a few exemplary heterocyclyls are shown in Table 3.

TABLE 3

Examples of heterocyclyls

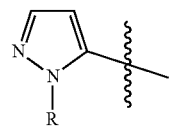
Substituted Pyrazolyl

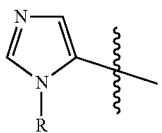
Substituted Imidazole

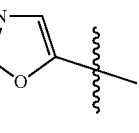
Oxazolyl

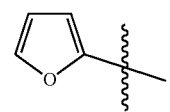
Furanyl

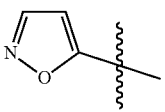
Isoxazolyl

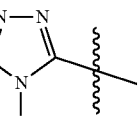
Substituted 1,2,4 Triazolyl

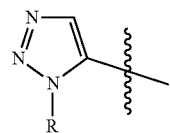
Substituted 1,2,3 Triazolyl

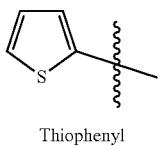 [SMILES: *c1cccs1]
Thiophenyl

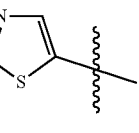
Thiazolyl

TABLE 3-continued

Examples of heterocyclyls

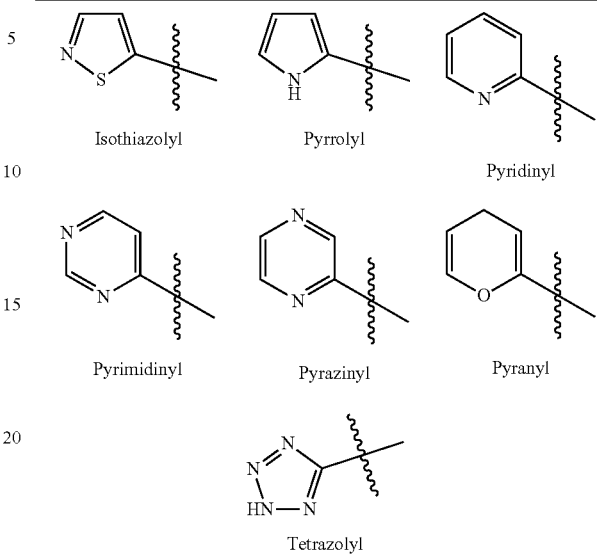

"Halo" or "halogen" refers to fluoro, chloro, bromo and iodo. Halo groups can be either fluoro or chloro.

"HCC" refers to hepatic cell carcinoma

"HDL" refers to high density lipoprotein.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, eg heteroalkyl, cycloalkyl, eg heterocycloalkyl, aryl, eg heteroaryl, cycloalkenyl, eg, heterocycloalkenyl, cycloheteroalkenyl, eg, heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine. An unsubstituted heteroatom refers to a pendant heteroatom such as an amine, hydroxyl and thiol. A substituted heteroatom refers to a heteroatom that is other than a pendant heteroatom.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

"Hydroxyl" refers to the radical —OH.

"KO" refers to knockout as used in the phrase knockout animals.

"MCD" refers to methionine-choline deficient diet

"NAFLD" refers to non-alcoholic fatty liver disease.

"NASH" refers to non-alcoholic steatohepatitis

"Nitro" refers to the radical —$NO_2$.

"Peptide" refers to a polyamino acid containing up to 2, 5, 10, or about 100 amino acid residues.

"Polypeptide" means polyamino acid containing from about 100 amino acid units to about 1,000 amino acid units, from about 100 amino acid units to about 750 amino acid units, or from about 100 amino acid units to about 500 amino acid units.

"ROP refers to an eye condition in infant's retinopathy of prematurity.

"SEM" refers to standard error of the mean

"Side-effect" means an undesirable adverse consequence of drug administration.

"Stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (eg an enantiomer, a diastereomer, or a geometric isomer). For example, Morrison and Boyd, Organic Chemistry, 1983, 4th ed., Allyn and Bacon, Inc., Boston, Mass., p 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, aralkyl, azido, carboxyl, cyano, cycloalkyl, substituted cycloalkyl, halogen, hydroxyl, imidate, keto, nitro, thioalkoxy, substituted thioalkoxy, thioaryloxy, thioketo, thiol, alkylthio, (substituted alkyl)thio, arylthio, (substituted aryl)thio, alkyl-S(O)—, aryl-S(O)—, alkyl-S(O)$_2$— and aryl-S(O)$_2$. Typical substituents include, but are not limited to, —X, —$R^8$ (with the proviso that $R^8$ is not hydrogen), —O—, =O, —$OR^8$, —$SR^8$, —S—, =S, —$NR^8R^9$, =$NR^8$, —$CX_3$, —$CF_3$, —CN, —OCN, —SCN, —NO, —$NO_2$, =$N_2$, —$N_3$, —S(O)$_2$O$^-$, —S(O)$_2$OH, —S(O)$_2R^8$, —OS(O$_2$)O$^-$, —OS(O)$_2R^8$, —P(O)(O—)$_2$, —P(O)($OR^8$)(O$^-$), —OP(O)($OR^8$)($OR^9$), —C(O)$R^8$, —C(S)$R^8$, —C(O)$OR^8$, —C(O)$NR^8R^9$, —C(O)O$^-$—, —C(S)$OR^8$, —$NR^{10}$C(O)$NR^8R^9$, —$NR^{10}$C(S)$NR^8R^9$, —$NR^{11}$C($NR^1$)$NR^8R^9$ and —C(NR)$NR^8R^9$, where X is independently a halogen.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"T2D" refers to type 2 diabetes.

"TG" refers to transgenic

"Thioalkoxy" refers to the group —S-alkyl.

"Thioaryloxy" refers to the group —S-aryl.

"Thioketo" refers to the group =S.

"Thiol" refers to the group —SH.

"UR" refers to uridine.

"UPase (Uridine phosphorylase)" refers in enzymology to a phosphorylase (EC 2.4.2.3) that catalyzes the chemical reaction: uridine+phosphate→uracil+alpha-D-ribose 1-phosphate. The two substrates of this enzyme are uridine and phosphate, whereas its two products are uracil and alpha-D-ribose 1-phosphate. This enzyme belongs to the family of glycosyltransferases, specifically the pentosyltransferases. The systematic name of this enzyme class is uridine: phosphate alpha-D-ribosyltransferase. Other names in common use include pyrimidine phosphorylase, UrdPase, UPH, and UPase. This enzyme participates in pyrimidine metabolism.

"Uridine Supplement" refers to either a formulated product containing UR or a formulated product containing a UR precursor such as UR monophosphate or acetylated UR that converts to UR in the body. The formulated product could be a solution, a capsule, a tablet or a cream. The product could be administered po, ip, sc, or iv. The UR supplement could be administered as part of a more complex mixture such as a nutritional supplement.

ip, po and sc are intraperitoneal, oral or subcutaneous dosing, respectfully. H&E is Haematoxylin & Eosin, a dye used to stain tissues. SD is standard deviation. SE is standard error. PBS is phosphate buffered saline. qd. and bid are daily and twice-a-day, respectfully.

One having ordinary skill in the art will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Methods of treating a subject for a liver condition, e.g., NAFLD, NASH, and/or DILI, are provided. Aspects of the methods include administering to the subject an effective amount of a UPase inhibitor, optionally in combination with a uridine active agent (e.g., uridine (UR), a UR pro-drug or a UR mimetic), such as supplemental uridine, to treat the subject for the liver condition. Also provided are compositions for use in practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing the subject invention, the subject methods are described first in greater detail, followed by a review of the various compositions, e.g., formulations and kits, that may find use in the subject methods, as well as a discussion of various representative applications in which the subject methods and compositions find use.

Methods

As summarized above, methods of treating, including prophylactically treating (e.g., preventing the occurrence of) a liver condition in a subject are provided. Aspects of the methods include administration to the subject of a UPase inhibitor, either alone or in combination with a uridine (UR) active agent (e.g., UR, a UR pro-drug or UR mimetic), to treat the subject for the liver condition. Where the UPase inhibitor is administered in combination, i.e., concurrently, with the UR active agent, the UPase inhibitor may be administered simultaneously with the UPase inhibitor. Alternatively, the UPase inhibitor and UR active agent may be administered sequentially, e.g., where the UPase inhibitor is administered before the UR active agent or the UPase in inhibitor is administered after the UR active agent. In such embodiments, the UPase inhibitor and the UR active agent can be administered at the same time, e.g., as two separate formulations, or combined into a single composition. Alternately, the UPase inhibitor and the UR active agent can be administered sequentially to the subject in different formulations. Regardless of whether the UPase inhibitor and the UR active agent are administered sequentially or simultaneously, or any effective variation thereof, the agents are considered to be administered together or in combination for purposes of the present invention. Routes of administration of the two agents may vary. Representative routes of administration are described below.

Subjects that are treated according to methods of the invention may be subjects suffering from, or suspected to suffer from, a liver condition, such as NAFLD, NASH or DILI. Treatment according to the disclosed methods can begin prophylactically for subjects at risk for liver disease or post diagnosis of a serious liver condition. Treatment can be carried out at intervals determined to be appropriate by those of skill in the art. For example, the administration can be carried out 1, 2, 3, 4 or more times/day. Ideally, treatment is expected to be qd chronically. Treatment can also be started before or at or near the same time as a drug associated with serious liver conditions.

The dose administered to an animal, particularly a human, in the context of the present invention should be sufficient to affect a prophylactic or therapeutic response in the animal over a reasonable time frame. One skilled in the art will recognize that dosage will depend on a variety of factors including the strength of the particular compound employed and the dosing regimen used, the condition of the animal, and the body weight of the animal, as well as the severity of the illness and the stage of the disease. The size of the dose will also be determined by the existence, nature, and extent of any adverse side-effects that might accompany the administration of a particular compound.

UPase Inhibitor

As summarized above, aspects of the invention include administration to the subject of a UPase inhibitor. UPase (UPh; EC 2.4.2.3) is a member of the pyrimidine nucleoside phosphorylase family of enzymes which catalyzes the phosphorolytic cleavage of the C—N glycoside bond of UR, with the formation of ribose 1-phosphate and uracil.[45] The UPase inhibitor is an agent that acts to modulate uridine plasma level in the subject, e.g., an agent that acts to elevate uridine (UR) plasma level in the subject. While the magnitude of any UR plasma level enhancement may vary, in some instances the magnitude of enhancement is 2-fold or greater, such as 5-fold or greater, 10-fold or greater, 15-fold or greater, 20-fold or greater, 25-fold or greater, or 50-fold or greater.

[45] Pizzorno G1, Cao D, Leffert J J, Russell R L, Zhang D, Handschumacher R E. Homeostatic control of uridine and the role of uridine phosphorylase: a biological and clinical update. Biochim Biophys Acta. 2002; 1587(2-3):133-44.

In some instances, the UPase inhibitor is an anhydronucleoside. Anhydronucleosides are analogs of natural nucleosides, often finding use as intermediates in the synthesis of nucleoside derivatives. They are characterized by having, in addition to the N-glycoside linkage, a covalent linkage either directly or via bridging atoms between the 2', 3', or 5' carbons of the sugar and a carbon, oxygen or nitrogen atom (other than the nitrogen of the glycoside bond) of the base. The anhydropyrimidines are characterized by a pyrimidine base that is covalently linked either directly or via bridging atoms between the 2', 3', or 5' carbons of the sugar and a carbon, oxygen or nitrogen atom (other than the nitrogen of the glycoside bond) of the pyrimidine base.

In some instances, the UPase inhibitor is a 2,2'-anhydropyrimidine or derivative thereof. In some embodiments, the 2,2'-anhydropyrimidine or derivative thereof is a compound of formula (I):

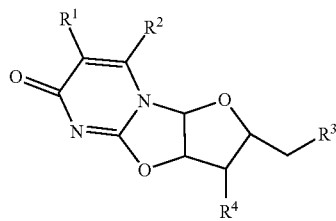

(I)

or the pharmaceutically acceptable salts, solvates, hydrates, and prodrug forms thereof, and stereoisomers thereof;

wherein:

each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, hydroxyl, halogen, azido, amino, substituted amino, carbohydrate, nucleic acid, amino acid, peptide, dye, fluorophore and polypeptide.

In certain embodiments, the compound is of formula (I), $R^1$, $R^2$, $R^3$ and $R^4$ are independently hydrogen, hydroxyl, heteroatom, $C_1$-$C_{18}$ alkyl, $C_1$-$C_{18}$ substituted alkyl, $C_1$-$C_{18}$ alkenyl, $C_1$-$C_{18}$ acyl, amino, substituted amino, wherein the alkyl, alkenyl or acyl is linear or branched, and optionally substituted with a hydroxyl, an ester and its derivatives, a carboxyl and its derivatives, a cycloalkyl, a heterocycloalkyl, an aryl, a heteroaryl, an aralkyl, a heteroatom, and possibly containing in chain or bridging heteroatoms such as nitrogen, oxygen and sulfur.

Examples of $R^1$ constituents of interest include, but are not limited to: hydrogen; hydroxyl; sulfhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, benzyloxy, imidate, alkylthio, (substituted alkyl)thio, arylthio, (substituted aryl)thio and the like; lower alkenyl containing 1 to 20 carbons such as vinyl and substituted vinyl, ethynyl and substituted ethynyl, where the substituted vinyl or substituted ethynyl designates substitution of the β position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like, or another aroyl such as benzyloxybenzyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or molpholino and the like.

Thus, in certain embodiments, $R^1$ is hydrogen, hydroxyl, sulfhydryl, amino, substituted amino, hydroxymethyl, monomethoxy, halogen, pseudohalogen, or a lower hydrocarbon (which hydrocarbon can be substituted or unsubstituted) containing from 1 to 20 atoms. In a particular embodiment, $R^1$ is a lower hydrocarbon selected from alkyl, substituted alkyl, alkenyl, alkanoyl, aryl, aroyl, aralkyl, or alkylamino. In a particular embodiment, $R^1$ is a lower hydrocarbon substituted with alkoxy, substituted alkoxy, imidate, arylthio, or (substituted aryl) thio. In other embodiments, $R^1$ is a lower alkyl selected from methyl, ethyl, propyl, isopropyl, butyl, isobutyl, tert-butyl and pentyl. In other embodiments, $R^1$ is a lower alkenyl selected from vinyl, substituted vinyl, ethynyl, or substituted ethynyl. In other embodiments, $R^1$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^1$ is lower aryl selected from phenyl, p-tolyl, p-chlorophenyl, p-aminophenyl, p-nitrophenyl, p-anisyl. In yet other embodiments, $R^1$ is a lower aroyl selected from benzoyl and naphthoyl. In other embodiments, $R^1$ is a lower aralkyl selected from benzyl, benzhydryl, p-chlorobenzyl, m-chlorobenzyl, p-nitrobenzyl, benzyloxybenzyl, or pentafluorobenzyl. In certain other embodiments, $R^1$ is a lower alkylamino is selected from monoalkylamino, monoaralkylamino, dialkylamino, diaralkylamino, and benzylamino.

Compounds of interest include, but are not limited to, those of formula (I) where $R^1$ is selected from hydrogen, fluorine, trifluoromethyl, methyl, ethyl, propyl, butyl, isopropyl, isobutyl, acetyl, propionyl, butyryl, 2-bromovinyl, phenyl, benzyl, benzoyl, benzyloxybenzyl, benzylamino, alkyloxyalkyl, benzyloxyalkyl, imidatealkyl, arylthio, and (substituted aryl) thio. Thus, in certain embodiments, the compound is of formula (I), and $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, benzyloxybenzyl, benzyl-NH—, $CH_3CH_2OCH_2$, benzyl-O—$CH_2$, $CH_3OCH_2$, $CH_3C(NH)$—O—$CH_2$, or $CH_3$-phenyl-O—$CH_2$.

Examples of $R^2$ constituents of interest include, but are not limited to: hydrogen; hydroxyl; sulfhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, and the like; lower alkenyl containing 1 to 20 carbons such as vinyl and substituted vinyl, ethynyl and substituted ethynyl, where the substituted vinyl or substituted ethynyl designates substitution of the β position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) and esters thereof of a main chain containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like, or another aroyl such as benzyloxybenzyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; lower aryloxy containing 1 to 20 carbons such as phenyloxy (ie, O-phenyl), benzyloxy (ie, O-benzyl), benzhydryloxy (ie, O-benzhydryl), p-chlorobenzyloxy (ie, O-(p-chlorobenzyl)), m-chlorobenzyloxy (ie, O-(m-chlorobenzyl)), p-nitrobenzyloxy (ie, O-(p-nitrobenzyl)), (4-benzyloxybenzyl)-oxy (ie, O-benzyloxybenzyl), or pentafluorobenzyloxy (ie, O-pentafluorobenzyl); esters of aryloxys, such as lower aryloxy (ie, O-aroyl) containing 1 to 20 carbons such as benzoyloxy (ie, O-benzoyl), diphenylacetyloxy (ie, O-diphenylacetyl), p-chlorobenzoyloxy (ie, O-(p-chlorobenzoyl)), m-chlorobenzoyloxy (ie, O-(m-chlorobenzoyl)), p-nitrobenzoyloxy (ie, O-(p-nitrobenzoyl)), (4-benzyloxybenzyl)-oxy (ie, O-benzyloxybenzyl), or pentafluorobenzyloxy (ie, O-pentafluorobenzoyl); amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or molpholino and the like.

Thus, in certain embodiments, $R^2$ is hydrogen, hydroxyl, sulfhydryl, amino, hydroxymethyl, monomethoxy, halogen, pseudohalogen, or a lower hydrocarbon (which hydrocarbon can be substituted or unsubstituted) containing from 1 to 20 atoms, and esters thereof. In a particular embodiment, $R^2$ is a lower hydrocarbon selected from alkyl, alkenyl, alkanoyl, aryl, aroyl, aryloxy, arylxy, aralkyl, or alkylamino. In other embodiments, $R^2$ is a lower alkyl selected from methyl, ethyl, propyl, isopropyl, butyl, isobutyl, tert-butyl and pentyl. In other embodiments, $R^2$ is a lower alkenyl selected from vinyl, substituted vinyl, ethynyl, or substituted ethynyl. In other embodiments, $R^2$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^2$ is lower aryl selected from phenyl, p-tolyl, p-chlorophenyl, p-aminophenyl, p-nitrophenyl, p-anisyl. In yet other embodiments, $R^2$ is a lower aroyl selected from benzoyl and naphthoyl. In other embodiments, $R^2$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^2$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^2$ is a lower aroyloxy selected from benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy. In certain other embodiments, $R^2$ is a lower alkylamino is selected from monoalkylamino, monoaralkylamino, dialkylamino, and diaralkylamino. Thus, in certain embodiments, $R^2$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest include, but are not limited to, those of formula (I) where $R^2$ is selected from hydrogen, fluorine, trifluoromethyl, methyl, ethyl, propyl, butyl, isopropyl, isobutyl, acetyl, propionyl, butyryl, 2-bromovinyl, phenyl, phenyloxy, benzyl, benzoyl, benzoyloxy and benzyloxybenzyl. Thus, in certain embodiments, the compound is of formula (I), and $R^2$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl.

In specific embodiments of interest, the compound is of formula (I), and $R^2$ is hydrogen, hydroxyl, or an O-linked substituent. This includes compounds of formula (I), where $R^2$ is H, OH or $C_6H_5C(O)O$.

Examples of $R^3$ of interest include, but are not limited to: hydrogen; hydroxyl; azido; sulfhydryl; halogen; pseudohalogen; lower alkyl containing 1 to 20 carbons such as methyl, ethyl, propyl, isopropyl, butyl, isobutyl, tert-butyl, pentyl and the like, including a substituted lower alkyl such as aminomethyl, hydroxymethyl, methoxy, ethyloxy, propyloxy, and the like; lower alkanoyl (acyl) including esters thereof of a main chain of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonoyl and the like; lower aryl such as phenyl, p-nitrophenyl, p-tolyl, p-anisyl, naphtyl and the like; lower aroyl (acyl radical of an aromatic acid) of 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like; lower aryloxy of 1 to 20 carbons such as phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy and the like; as well as esters of aryloxys, such as lower aroyloxy (O-aroyls) of 1 to 20 carbons such as benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy and the like. $R^3$ may also be adamantyl, or substituted adamantyl.

Thus, in certain embodiments, $R^3$ is hydrogen, hydroxyl, azido, sulfhydryl, hydroxymethyl, halogen, or pseudohalogen. In other embodiments, $R^3$ is a lower hydrocarbon selected from alkyl, alkanoyl, aryl, aroyl, aryloxy, aroyloxy, or aralkyl. In other embodiments, $R^3$ is a lower alkyl selected from methyl, ethyl, propyl, isopropyl, butyl, isobutyl, tert-butyl and pentyl. In other embodiments, $R^3$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonoyl. In other embodiments, $R^3$ is a lower aryl selected from phenyl, p-tolyl, p-chlorophenyl, p-aminophenyl, p-nitrophenyl, p-anisyl and the like. In other embodiments, $R^3$ is a lower aroyl selected from benzoyl and naphthoyl. In yet other certain embodiments, $R^3$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^3$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^3$ is a lower aroyloxy selected from benzoyloxy, diphenylacetyloxy, p-chlorobenzoyloxy, m-chlorobenzoyloxy, p-nitrobenzoyloxy, (4-benzyloxybenzyl)-oxy, or pentafluorobenzyloxy. Thus, in certain embodiments, $R^3$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest are those of formula (I) where $R^3$ is hydrogen, hydroxyl, halogen, azido, or an O-linked substituent. This includes compounds of formula (I) where $R^3$ is selected from hydrogen, hydroxyl, n-butoxy, isobutyloxy, t-butyloxy, phenyloxy, benzyloxy, benzoyloxy, and pentafluorobenzyloxy. Thus, in certain embodiments, the compound is of formula (I), and $R^3$ is selected from H, OH, $CH_3CH_2CH_2CH_2O$, $(CH_3)_2CH_2CH_2O$, $(CH_3)_3CO$, $C_6H_5O$, benzoyloxy, and pentafluorobenzyloxy.

In specific embodiments of interest, the compound is of formula (I), where $R^3$ is H, OH, F, Cl, Br, I, $N_3$, or $C_6H_5C(O)O$. Of special interest is a compound of formula (I), where $R^3$ is OH, or O-acyl (for example, an ester such as $C_6H_5C(O)O$).

Examples of $R^4$ include, but are not limited to: hydrogen; hydroxyl; sulfhydryl; halogen such as fluorine, chlorine, bromine or iodine; amino or lower alkylamino. $R^4$ also is exemplified by lower alkyl, with acyl groups which may be lower alkanoyl groups of 1 to 7 carbon atoms such as formyl, acetyl, propionyl, isopropionyl, butyryl, isobutyryl, tert-butyryl and the like, and esters thereof. Thus, $R^4$ can also be aroyl (and esters thereof such as O-linked aroyls, ie, O-arolys or arolyoxy) such as benzoyl and naphthoyl wherein the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl and the like. Accordingly, in certain embodiments, $R^4$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Thus, in certain embodiments, $R^4$ is hydrogen; hydroxyl; sulfhydryl; halogen, amino aminomethyl, or aminodimethyl. In other embodiments, $R^4$ is a lower alkyl, acyl, aroyl, or aroyloxy. This includes a specific embodiment, where the compound of formula (I) is one where $R^4$ is hydrogen, flourine, hydroxyl, amino, aminomethyl, aminodimethyl, t-butyloxy, phenyloxy or benzoyloxy (for example, a compound of formula (I), where $R^4$ is H, F, OH, $NH_2$, $NHCH_3$, $N(CH_3)_2$, $(CH_3)_3CO$, $C_6H_5O$ or $C_6H_5C(O)O$).

Compounds of particular interest are those of formula (I) where $R^4$ is hydrogen, hydroxyl, or an O-linked substituent. In specific embodiments, the compound is of formula (I), where $R^4$ is H, OH or $C_6H_5C(O)O$. Of special interest is a compound of formula (I), where $R^4$ is OH, or O-acyl (for example, an ester such as $C_6H_5C(O)O$).

Of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl, and where $R^3$ and $R^4$ are each hydroxyl. These include the compounds: 2,2'-anhydrouridine; 2,2'-anhydro-5-fluorouridine; 2,2'-anhydro-5-trifluoromethyluridine; 2,2'-anhydro-5-methyluridine; 2,2'-anhydro-5-ethyluridine; 2,2'-anhydro-5-propyluridine; 2,2'-anhydro-5-isopropyluridine; 2,2'-anhydro-5-isobutyluridine; 2,2'-anhydro-5-methylacyluridine; 2,2'-anhydro-5-propylacyluridine; 2,2'-anhydro-5-(2-bromovinyl)-uridine; 2,2'-anhydro-5-phenyluridine; 2,2'-anhydro-5-benzoyluridine; 2,2'-anhydro-5-benzoyluridine; and 2,2'-anhydro-5-(benzyloxybenzyl)-uridine. Of special interest is 2,2'-anhydro-5-methyluridine, or the pharmaceutically acceptable salts, solvates, hydrates, and prodrug forms thereof, and stereoisomers thereof.

Additional compounds of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is hydroxyl, and $R^4$ is benzoyloxy. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenyluridine; 3'-O-benzoyl-2,2'-anhydro-5-benzoyluridine; 3'-O-benzoyl-2,2'-anhydro-5-benzoyluridine; and 3'-O-benzoyl-2,2'-anhydro-5-(benzyloxybenzyl)-uridine. Of specific interest is 3'-O-benzoyl-2,2'-anhydro-5-methyluridine, or the pharmaceutically acceptable salts, solvates, hydrates, and prodrug forms thereof, and stereoisomers thereof.

Also of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is benzoyloxy, and $R^4$ is hydroxyl. These include the compounds: 5'-O-benzoyl-2,2'-anhydrouridine; 5'-O-benzoyl-2,2'-anhydro-5-fluorouridine; 5'-O-benzoyl-2,2'- anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzoyluridine; 5'-O-benzoyl-2,2'-anhydro-5-benzoyluridine; and 5'-O-benzoyl-2,2'-anhydro-5-(benzyloxybenzyl)-uridine. Of specific interest is 5'-O-benzoyl-2,2'-anhydro-5-methyluridine, or the pharmaceutically acceptable salts, solvates, hydrates, and prodrug forms thereof, and stereoisomers thereof.

The 2,2'-anhydropyrimidine compounds of the invention may be in compositions that contain single stereoisomers, mixtures of stereoisomers, as well various derivatives thereof that can occur as equilibrium mixtures of tautomers. For instance, 2,2'-anhydropyrimidines according to formula (I) include four stereo centers with respect to the furano ring, which includes the α and β anomers, and the L or D mirror image configurations. Examples of stereoisomers of the 2,2'-anhydropyrimidine compounds of the invention are the β-D-isomer, β-L-isomer, α-D-isomer, and α-L-isomer, as well as tautomers and mixtures including α,β-D-isomers, α,β-L-isomers, α-DL-isomers, and β-DL-isomers. Thus, in one embodiment, compositions are provided that consists essentially of a stereoisomer of a 2,2'-anhydropyrimidine that is a β-D-isomer, β-L-isomer, α-D-isomer, or an α-L-isomer.

Stereoisomers of particular interest include: 2,2'-anhydro-1-(ρ-D-arabinofuranosyl)uracil; 2,2'-anhydro-1-(β-D-arabinofuranosyl)-5-fluorouracil; 2,2'-anhydro-1-(β-D-arabinofuranosyl)-5-trifluoromethyluracil; 2,2'-anhydro-1-(β-D-arabinofuranosyl)-5-methyluracil; 2,2'-anhydro-1-(β-D-arabinofuranosyl)-5-ethyluracil; 2,2'-anhydro-1-(β-D-arabinofuranosyl)-5-n-propyluracil; 2,2'-anhydro-1-(β-D-arabinofuranosyl)-5-isopropyluracil; 2,2'-anhydro-1-(β-D-arabinofuranosyl)-5-isobutyluracil; 2,2'-anhydro-1-(β-D-arabinofuranosyl)-5-methyacyluracil; 2,2'-anhydro-1-(β-D-arabinofuranosyl)-5-propylacyluracil; 2,2'-anhydro-1-(β-D-arabinofuranosyl)-5-(2-bromovinyl)uracil; 2,2'-anhydro-1-(β-D-arabinofuranosyl)-5-phenyluracil; 2,2'-anhydro-1-(β-D-arabinofuranosyl)-5-benzyluracil; 2,2'-anhydro-1-(β-D-arabinofuranosyl)-5-benzoyluracil; and 2,2'-anhydro-1-(β-D-arabinofuranosyl)-5-(3-benzyloxybenzyl)uracil. Further stereoisomers of interest include: 3'-O-benzoyl-2,2'-anhydro-1-(β-D-arabinofuranosyl)uracil; 3'-O-benzoyl-2,2'-anhydro-1-(β-D-arabinofuranosyl)-5-fluoruracil; 3'-O-benzoyl-2,2'-anhydro-1-(β-D-arabinofuranosyl)-5-trifluoromethyluracil; 3'-O-benzoyl-2,2'-anhydro-1-(β-D-arabinofuranosyl)-5-methyluracil; 3'-O-benzoyl-2,2'-anhydro-1-(β-D-arabinofuranosyl)-5-ethyluracil; 3'-O-benzoyl-2,2'-anhydro-1-(β-D-arabinofuranosyl)-5-n-propyluracil; 3'-O-benzoyl-2,2'-anhydro-1-(β-D-arabinofuranosyl)-5-isopropyluracil; 3'-O-benzoyl-2,2'-anhydro-1-(β-D-arabinofuranosyl)-5-isobutyluracil; 3'-O-benzoyl-2,2'-anhydro-1-(β-D-arabinofuranosyl)-5-methyacyluracil; 3'-O-benzoyl-2,2'-anhydro-1-(β-D-arabinofuranosyl)-5-propylacyluracil; 3'-O-benzoyl-2,2'-anhydro-1-(β-D-arabinofuranosyl)-5-(2-bromovinyl)uracil; 3'-O-benzoyl-2,2'-anhydro-1-(β-D-arabinofuranosyl)-5-phenyluracil; 3'-O-benzoyl-2,2'-anhydro-1-(β-D-arabinofuranosyl)-5-benzyluracil; 3'-O-benzoyl-2,2'-anhydro-1-(β-D-arabinofuranosyl)-5-benzoyluracil; and 3'-O-benzoyl-2,2'-anhydro-1-(β-D-arabinofuranosyl)-5-(3-benzyloxybenzyl)uracil. Additional stereoisomers of interest include: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzoyluracil; and 5'-O-benzoyl-2,2'-anhydro-1-(β-D-arabinofuranosyl)-5-(3-benzyloxybenzyl)uracil.

Examples of other analogs or derivatives of the 2,2'-anhydropyrimidines of the invention, and stereoisomers thereof include: 3'-O-acetyl-2,2'-anhydro-5-propyluridine (3'-O-acetyl-2,2'-anhydro-1-(β-D-arabinofuranosyl)-5-propyluracil); and 3'-O-acetyl-2,2'-anhydro-5-isopropyluridine (3'-O-acetyl-2,2'-anhydro-1-(1-D-arabinofuranosyl)-5-isopropyluracil); as well as the 2,2'-anhydrocytidines, and analogs and derivatives thereof, of which the stereoisomer 2,2'-anhydro-1-(β-D-arabinofuranosyl)cytosine is one example.

As noted above, stereoisomers and the various 2,2'-anhydropyrimidines of particular interest are those which exhibit improved activity on a molar basis. Such compounds can be readily selected for this purpose by comparing against a matrix of compounds of particular interest, such as those illustrated in Table 4 (where the compound is of formula (I)).

TABLE 4

| | The compound is of formula (I) | | | | |
|---|---|---|---|---|---|
| Compound | Stereoisomer | $R^1$ | $R^2$ | $R^3$ | $R^4$ |
| I-a | β-D-isomer | H | H | OH | OH |
| I-b | β-D-isomer | $CH_3$ | H | OH | OH |
| I-c | β-D-isomer | $CH_3CH_2$ | H | OH | OH |
| I-d | β-D-isomer | $CH_3CH_2CH$ | H | OH | OH |
| I-e | β-D-isomer | $BrCH=CH$ | H | OH | OH |
| I-f | β-D-isomer | $C_6H_5CH_2$ | H | OH | OH |
| I-g | β-D-isomer | H | H | $C_6H_5C(O)O$ | OH |
| I-h | β-D-isomer | $CH_3$ | H | $C_6H_5C(O)O$ | OH |
| I-i | β-D-isomer | $CH_3CH_2$ | H | $C_6H_5C(O)O$ | OH |

TABLE 4-continued

The compound is of formula (I)

| Compound | Stereoisomer | $R^1$ | $R^2$ | $R^3$ | $R^4$ |
|---|---|---|---|---|---|
| I-j | β-D-isomer | $CH_3CH_2CH$ | H | $C_6H_5C(O)O$ | OH |
| I-k | β-D-isomer | $BrCH=CH$ | H | $C_6H_5C(O)O$ | OH |
| I-l | β-D-isomer | $C_6H_5CH_2$ | H | $C_6H_5C(O)O$ | OH |
| I-m | β-D-isomer | $F—C_6H_5CH_2$ | H | OH | OH |
| I-n | β-D-isomer | $NO_2—C_6H_5CH_2$ | H | OH | OH |
| I-o | β-D-isomer | $NH_2—C_6H_5CH_2$ | H | OH | OH |
| I-p | β-D-isomer | $Cl—C_6H_5CH_2$ | H | OH | OH |
| I-q | β-D-isomer | Alkyl-$C_6H_5CH_2$ | H | OH | OH |
| I-r | β-D-isomer | Methoxy-$C_6H_5CH_2$ | H | OH | OH |
| I-s | β-D-isomer | Thiol-$C_6H_5CH_2$ | H | OH | OH |
| I-t | β-D-isomer | $F—C_6H_5CH_2$ | H | $C_6H_5C(O)O$ | OH |
| I-u | β-D-isomer | $NO_2—C_6H_5CH_2$ | H | $C_6H_5C(O)O$ | OH |
| I-v | β-D-isomer | $NH_2—C_6H_5CH_2$ | H | $C_6H_5C(O)O$ | OH |
| I-w | β-D-isomer | $Cl—C_6H_5CH_2$ | H | $C_6H_5C(O)O$ | OH |
| I-x | β-D-isomer | Alkyl-$C_6H_5CH_2$ | H | $C_6H_5C(O)O$ | OH |
| I-y | β-D-isomer | Methoxy-$C_6H_5CH_2$ | H | $C_6H_5C(O)O$ | OH |
| I-z | β-D-isomer | Thiol-$C_6H_5CH_2$ | H | $C_6H_5C(O)O$ | OH |
| I-a' | β-D-isomer | H | OH | H | OH |
| I-b' | β-D-isomer | $CH_3$ | OH | H | OH |
| I-c' | β-D-isomer | $CH_3CH_2$ | OH | H | OH |
| I-d' | β-D-isomer | $CH_3CH_2CH$ | OH | H | OH |
| I-e' | β-D-isomer | $BrCH=CH$ | OH | H | OH |
| I-f' | β-D-isomer | $C_6H_5CH_2$ | OH | H | OH |
| I-g' | β-D-isomer | H | $C_6H_5C(O)O$ | H | OH |
| I-h' | β-D-isomer | $CH_3$ | $C_6H_5C(O)O$ | H | OH |
| I-I' | β-D-isomer | $CH_3CH_2$ | $C_6H_5C(O)O$ | H | OH |
| I-j' | β-D-isomer | $CH_3CH_2CH$ | $C_6H_5C(O)O$ | H | OH |
| I-k' | β-D-isomer | $BrCH=CH$ | $C_6H_5C(O)O$ | H | OH |
| I-l' | β-D-isomer | $C_6H_5CH_2$ | $C_6H_5C(O)O$ | H | OH |
| I-m' | β-D-isomer | $F—C_6H_5CH_2$ | OH | H | OH |
| I-n' | β-D-isomer | $NO_2—C_6H_5CH_2$ | OH | H | OH |
| I-o' | β-D-isomer | $NH_2—C_6H_5CH_2$ | OH | H | OH |
| I-p' | β-D-isomer | $Cl—C_6H_5CH_2$ | OH | H | OH |
| I-q' | β-D-isomer | Alkyl-$C_6H_5CH_2$ | OH | H | OH |
| I-r' | β-D-isomer | Methoxy-$C_6H_5CH_2$ | OH | H | OH |
| I-s' | β-D-isomer | Thiol-$C_6H_5CH_2$ | OH | H | OH |
| I-t' | β-D-isomer | $F—C_6H_5CH_2$ | $C_6H_5C(O)O$ | H | OH |
| I-u' | β-D-isomer | $NO_2—C_6H_5CH_2$ | $C_6H_5C(O)O$ | H | OH |
| I-v' | β-D-isomer | $NH_2—C_6H_5CH_2$ | $C_6H_5C(O)O$ | H | OH |
| I-w' | β-D-isomer | $Cl—C_6H_5CH_2$ | $C_6H_5C(O)O$ | H | OH |
| I-x' | β-D-isomer | Alkyl-$C_6H_5CH_2$ | $C_6H_5C(O)O$ | H | OH |
| I-y' | β-D-isomer | Methoxy-$C_6H_5CH_2$ | $C_6H_5C(O)O$ | H | OH |
| I-z' | β-D-isomer | Thiol-$C_6H_5CH_2$ | $C_6H_5C(O)O$ | H | OH |

As mentioned above, the compounds in Table 4 are illustrative but not limiting. For example, $R^4$ can be not only hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O and other combinations of the structural elements such as described herein, as well as other stereochemical orientations, are also possible.

In certain embodiments, acyl derivatives of the 2,2'-anyhydropyrimidines of formula (I) are of interest. Thus, compounds of formula (I) include those in which $R^1$, $R^2$, $R^3$ and $R^4$ are as defined above, wherein at least one of $R^2$, $R^3$ and $R^4$ is an acyl derivative. By "acyl derivative" is intended a derivative of a 2,2'-anyhydropyrimidine of formula (I) in which at least one of $R^2$, $R^3$ and $R^4$ is a substantially nontoxic organic acyl substituent obtainable from a carboxylic acid that is attached to a hydroxyl group on the ribose or pyrimidine ring of formula (I) through an ester linkage.

Acyl derivatives of a 2,2'-anyhydropyrimidine compound of formula (I) include those in which $R^1$ is as defined above, and each $R^2$, $R^3$ and $R^4$ is independently hydrogen, hydroxyl or an acyl radical, with the proviso that at least one of $R^2$, $R^3$ and $R^4$ is not hydrogen. In another embodiment, the acyl derivative of a 2,2'-anyhydropyrimidine is a compound of formula (I) in which $R^1$ and $R^2$ are as defined above, with the proviso that $R^2$ is other than hydrogen, and each $R^3$ and $R^4$ is independently hydroxyl or an acyl radical. In one embodiment, the acyl derivative of a 2,2'-anyhydropyrimidine is a compound of formula (I) in which $R^1$ is as defined above, $R^2$ is hydrogen, and each $R^3$ and $R^4$ is independently hydroxyl or an acyl radical. Of particular interest, is an acyl derivative of a 2,2'-anyhydropyrimidine compound of formula (I), wherein $R^1$ is methyl, $R^2$ is hydrogen, and each $R^3$ and $R^4$ is independently hydroxyl or an acyl radical. Also of interest is an acyl derivative of a 2,2'-anyhydropyrimidine compound of formula (I), wherein $R^1$ is methyl, $R^2$ is hydrogen, and each $R^3$ and $R^4$ is an acyl radical.

In general, the ester linkage(s) of an acyl derivative of formula (I) are cleavable under physiological conditions, either in vitro, such as in a cell-based system, and/or in vivo, such as through metabolism in a body. Thus, in certain embodiments, the acyl radical is a radical of a metabolite. Such acyl substituents include, but are not limited to, those derived from acetic acid, fatty acids, amino acids, lipoic acid, glycolic acid, lactic acid, enolpyruvic acid, pyruvic acid, orotic acid, acetoacetic acid, beta-hydroxybutyric acid, creatinic acid, succinic acid, fumaric acid, adipic acid, benzoic acid and p-aminobenzoic acid. Particular acyl substituents of interest are compounds which are normally present in the body, either as dietary constituents or as intermediary metabolites, and which are essentially nontoxic when cleaved from the 2,2'-anyhydropyrimidine compound of interest in vivo.

Of particular interest are compositions comprising a 3'-O-acyl-2,2'-anhydropyrimidine or derivative thereof. For example, acyl derivatives of interest are those that include a 2,2'-anyhydropyrimidine compound of formula (I), where each $R^1$, $R^2$ and $R^3$ is independently selected from selected from hydrogen, hydroxyl, sulfhydryl, amino, hydroxymethyl, methoxy, halogen, pseudohalogen, and a substituted or unsubstituted lower hydrocarbon containing 1 to 20 carbons, such as a lower hydrocarbon selected from alkyl, alkenyl, alkanoyl, aryl, aroyl, aralkyl and alkylamino, and esters thereof, and where $R^4$ is an O-acyl radical.

In certain embodiments, the acyl derivatives include a 2,2'-anyhydropyrimidine compound of formula (I), where $R^4$ is an O-acyl radical, and where the O-acyl radical comprises 1 to 10 carbon atoms, such as an O-acyl radical selected from aroyloxy, aralkyloxy, heteroaryoloxy, and cycloalkyloxy.

Accordingly, acyl derivatives of a 2,2'-anyhydropyrimidine compound of formula (I) include 3'-O-acyl-2,2'-anyhdropyrimidines, 5'-O-acyl-2,2'-anyhdropyrimidines, 3',5'-O-acyl-2,2'-anyhdropyrimidines, and derivatives thereof. For example, 3'-O-acyl-2,2'-anhydropyrimidines or derivatives thereof include 3'-O-aroyl-2,2'-anyhdropyrimidines, such as a 3'-O-aroyl-2,2'-anhydrouridine or derivative thereof. An example of particular interest is 3'-O-benzoyl-2,2'-anhydrouridine or derivative thereof, such as 3'-O-benzoyl-2,2'-anhydro-5-methyluridine. Also of interest is a compound in which the 3'-O-benzoyl-2,2'-anhydro-5-methyluridine is the stereoisomer 3'-O-benzoyl-2,2'-anhydro-1-(β-D-arabinofuranosyl)-5-methyluracil.

In some embodiments, acyl derivatives of a 2,2'-anyhdropyrimidine compound of formula (I) include those where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzyloxybenzyl, or acyl radical, and where each $R^3$ and $R^4$ is independently hydroxyl or an acyl radical. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzoyluridine; and 3'-O-benzoyl-2,2'-anhydro-5-(benzyloxybenzyl)-uridine; 5'-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzoyluridine; 5'-O-benzoyl-2,2'-anhydro-5-benzoyluridine; and 5'-O-benzoyl-2,2'-anhydro-5-(benzyloxybenzyl)-uridine; 3',5'-O-benzoyl-2,2'-anhydrouridine; 3',5'-O-benzoyl-2,2'-anhydro-5-fluorouridine; 3',5'-O-benzoyl-2,2'-anhydro-5-trifluoromethyluridine; 3',5'-O-benzoyl-2,2'-anhydro-5-methyluridine; 3',5'-O-benzoyl-2,2'-anhydro-5-ethyluridine; 3',5'-O-benzoyl-2,2'-anhydro-5-propyluridine; 3',5'-O-benzoyl-2,2'-anhydro-5-isopropyluridine; 3',5'-O-benzoyl-2,2'-O-anhydro-5-isobutyluridine; 3',5'-O-benzoyl-2,2'-anhydro-5-methylacyluridine; 3',5'-O-benzoyl-2,2'-anhydro-5-propylacyluridine; 3',5'-O-benzoyl-2,2'-anhydro-5-(2-bromovinyl)-uridine; 3',5'-O-benzoyl-2,2'-anhydro-5-phenylluridine; 3',5'-O-benzoyl-2,2'-anhydro-5-benzoyluridine; 3',5'-O-benzoyl-2,2'-anhydro-5-benzoyluridine; and 3',5'-O-benzoyl-2,2'-anhydro-5-(benzyloxybenzyl)-uridine; or the pharmaceutically acceptable salts, solvates, hydrates, and prodrug forms thereof, and stereoisomers thereof.

Of specific interest is 3'-O-benzoyl-2,2'-anhydro-5-methyluridine, 5'-O-benzoyl-2,2'-anhydro-5-methyluridine, and 3',5'-O-benzoyl-2,2'-anhydro-5-methyluridine, or the pharmaceutically acceptable salts, solvates, hydrates, and prodrug forms thereof, and stereoisomers thereof. Of specific interest are the β-D-arabinofuranosyl isomers of these compounds, or the pharmaceutically acceptable salts, solvates, hydrates, and prodrug forms thereof.

In another embodiment, compounds according to formula (I) of specific interest are those where $R^1$ and $R^4$ are as defined above, and $R^2$ and/or $R^3$ is a cyclic hydrocarbyl. By "cyclic hydrocarbyl" is intended a hydrocarbon-based ring structure having from 3 to about 10 carbon atoms, and having a single cyclic ring or multiple condensed rings that may be substituted. Cyclic hydrocarbyls of interest are selected from aryl, aralkyl, aryloxy, aroyl, aroyloxy, heteroaryl, heteroaryloxy, heteroaryoloxy, cycloalkyl, cycloalkyloxy and cycloalkyloxy. Thus, cyclic hydrocarbyls of special interest are O-linked to the ribose or pyrimidine ring of formula (I). Compounds where $R^2$ and/or $R^3$ is a cyclic hydrocarbyl exhibit improved activity on a molar basis.

Accordingly, certain compounds of the invention comprise a 5'-O-(cyclic hydrocarbyl)-2,2'-anhydropyrimidine or derivative thereof. This embodiment includes 5'-O-(cyclic hydrocarbyl)-2,2'-anhydro-5($R^5$)-uridine or derivatives thereof, where $R^5$ is $R^1$ (eg, $R^5=R^1$ where "5($R^5$)" refers to, and is the same as, $R^1$ of formula (I)).

A compound of interest is 5'-O-aryl-2,2'-anhydropyrimidine or derivative thereof, of which various 2,2'-anhydrouridine derivatives are of included. This includes compounds where the 5'-O-aryl-2,2'-anhydropyrimidine is a 5'-O-aroyl-2,2'-anhydropyrimidine, such as: 5'-O-benzoyl-2,2'-anhydropyrimidine; 5'-O-chlorobenzyl-2,2'-anhydropyrimidine; 5'-O-nitrobenzyl-2,2'-anhydropyrimidine; 5'-O-hydroxybenzyl-2,2'-anhydropyrimidine, and the like.

In one embodiment, compounds that exhibit improved activity on a molar basis or improved specificity with respect to not interfering with fluorouracil therapy efficacy are the 5'-O-aryl-2,2'-anhydrouridines, 5'-O-aroyl-2,2'-anhydrouridines, and derivatives thereof, such as 5'-O-aryl-2,2'-anhydro-5($R^4$)-uridine, 5'-O-aroyl-2,2'-anhydro-5($R^4$)-uridine, and their derivatives. Examples include 5'-O-aryl-2,2'-anhydro-5-methyl-uridine; 5'-O-aryl-2,2'-anhydro-5-ethyl-uridine; 5'-O-aryl-2,2'-anhydro-5-propyl-uridine; 5'-O-aryl-2,2'-anhydro-5-benzyl-uridine; and 5'-O-aryl-2,2'-anhydro-5-(2-bromovinyl)-uridine; and derivatives thereof. Examples also include 5'-O-aroyl-2,2'-anhydro-5-methyl-uridine; 5'-O-aroyl-2,2'-anhydro-5-ethyl-uridine; 5'-O-aroyl-2,2'-anhydro-5-propyl-uridine; 5'-O-aroyl-2,2'-anhydro-5-benzyl-uridine; and 5'-O-aroyl-2,2'-anhydro-5-(2-bromovinyl)-uridine; and derivatives thereof. Compounds of specific interest include 5'-O-benzoyl-2,2'-anhydro-5-($R^4$)-uridines, such as 5'-O-benzoyl-2,2'-anhydro-5-methyl-uridine; 5'-O-benzoyl-2,2'-anhydro-5-ethyl-uridine; 5'-O-benzoyl-2,2'-anhydro-5-propyl-uridine; 5'-O-benzoyl-2,2'-anhydro-5-benzyl-uridine; and 5'-O-benzoyl-2,2'-anhydro-5-(2-bromovinyl)-uridine. Stereoisomers of interest include the 5'-O-(cyclic hydrocarbyl)-2,2'-anhydropyrimidines which are the β-D-isomers. Examples include, but are not limited to: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzoyluracil; and 5'-O-benzoyl-2,2'-anhydro-1-(β-D-arabinofuranosyl)-5-(3-benzyloxybenzyl)uracil.

As noted above, also of interest are analogues/derivatives of the above compounds.

The 2,2'-anhydropyrimidine and derivatives thereof described above are commercially available or can be conventionally prepared by techniques known to one of skill in the art. For example, representative patents describing various 2,2'-anhydropyrimidine and derivatives, including intermediates and precursors, analysis, as well as the synthesis/preparation thereof, include U.S. Pat. Nos. 3,975,367; 4,145,531; 4,230,698; 4,247,544; 4,544,740; 4,604,382; 4,613,604; 4,681,933; 4,841,039; 4,916,122; 4,987,224; 5,008,384; 5,077,280; 5,084,445; 5,141,943; 5,190,926; 5,212,293; 5,278,167; 5,384,396; 5,455,339; 5,476,855; 5,596,093; 5,610,292; 5,721,241; 5,723,449; 5,739,314; 5,760,202; 5,889,013; 5,861,493; 6,060,592; 6,090,932; 6,222,025; 6,369,040; 6,642,367; 6,670,461; 6,867,290; and 7,176,295; the disclosures of which are herein incorporated by reference.

Uridine phosphorylase (UPase) inhibitors also include, but are not limited to: benzylacyclouridine, benzyloxyacylouridine, aminomethyl-benzylacylouridine, aminomethylbenzyloxybenzylacyclouridine, hydroxymethyl-benzylacyclouridine, hydroxymethyl-benzyloxybenzyl acyclouridine, and the like; derivatives of 5-benzylbarbiturate, such as 5-benzyloxybenzyl barbiturate; 5-benzyloxybenzyl-1-(1-hydroxy-2-ethoxy)methyl) barbiturate; 5-benzyloxybenzylacetyl-1-(1-hydroxy-2-ethoxy) methyl) barbiturate; 5-benzyloxybenzyl-1-(1,3-dihydroxy 2-propoxy)methyl barbiturate; 5-benzyloxybenzyl-1-(1-hydroxy, 3-amino-2-propoxy)methyl) barbiturate; 5-benzyloxybenzyl-1-(2-(3-carboxypropionyloxy)ethoxy) methyl) barbiturate; 5-benzyl-1-(1-hydroxy-2-ethoxy) methyl) barbiturate; 5-methoxybenzylacetyl barbiturate; 5-benzyl-1-(1,3-dihydroxy-2-propoxy)methyl) barbiturate; 5-benzyl-1-(1-hydroxy, 3-amino-2-propoxy)methyl)barbiturate; and 5-benzyl-1-(2-(3-carboxypropionyloxy)ethoxy)methyl) barbiturate, and the like. Upase inhibitors which may be employed in embodiments of the invention include, but are not limited to, those described in U.S. Pat. Nos. 5,723,449; 5,141,943; 5,077,280; and 4,613,604; the disclosures of which compounds are incorporated herein by reference.

Uridine (UR) Active Agents

As summarized above, in some embodiments the UPase inhibitor is administered to the subject in combination with a UR active agent (e.g., uridine (UR), a UR pro-drug or a UR mimetic). Uridine is a nucleoside that is formed when uracil is attached to a ribose ring (also known as a ribofuranose) via a β-$N_1$-glycosidic bond. Uridine is available in phosphorylated form, i.e., uridine-5'-monophosphate (also known as 5'-uridylic acid and UMP), uridine 5'-monophosphate tris salt, uridine 5'-monophosphate salt dihydrate, uridine 5'-monophosphate salt solution, uridine 5'-monophosphate salt hydrate, uridine$^{13}C_9$, $^{15}N_2$ 5'-monophosphate sodium salt solution, uridine-$^{15}N_2$ 5'-monophosphate sodium salt solution, uridine 5'-monophosphate trisodium salt hydrate, uridine-$N_2$ 5'-monophosphate sodium salt solution, uridine-5'-diphosphate (UDP), uridine 5'-diphosphate tris salt, uridine 5'-diphosphate salt dihydrate, uridine 5'-diphosphate salt solution, uridine 5'-diphosphate salt hydrate, uridine$^{13}C_9$, $^{15}N_2$ 5'-diphosphate sodium salt solution, uridine-5'-triphosphate (UTP), UTPγS, MRS2498, uridine 5'-triphosphate tris salt, uridine 5'-triphosphate salt dihydrate, uridine 5'-triphosphate salt solution, uridine 5'-triphosphate salt hydrate, uridine$^{13}C_9$, $^{15}N_2$ 5'-5'-triphosphate sodium salt solution, 2-diuridine tetraphosphate, thio-UTP tetrasodium salt, denufosol tetrasodium, or UTP.gamma.S trisodium salt, prodrugs known in the art as triacetyluridine (TAU) or uridine triacetate (PN501), acyl derivatives of uridine such as those described in U.S. Pat. No. 7,582,619 (i.e., 2',3',5'-tri-0-pyruvyluridine), 2,2'-anhydro-5-ethyluridine, 5-ethyl-2-deoxyuridine, and acyclouridine compounds such as 5-benzyl substituted acyclouridine congeners including, e.g., benzylacyclouridine, benzyloxybenzylacyclouridine, aminomethyl-benzylacyclouridine, aminomethylbenzyloxy-benzylacyclouridine, hydroxymethyl-benzyloxybenzylacyclouridine (see also, WO89/09603 and WO91/16315), and in dietary supplements such as Mitocnol and NucleomaxX, derived from sugar cane extract.

UR and sources thereof include, but are not limited to: meat products, such as fish, pig and cow liver and pancreas, and the like; fungi related products, such as brewer's yeast, beer, mushrooms, and the like; vegetable products, such as sugarcane, tomatoes, oats, algae, broccoli and the like; salts, such as UR phosphates, acylated UR, and the like. UR and sources thereof which may be employed in embodiments of the invention include, but are not limited to, those described in U.S. Pat. Nos. 9,579,337; 6,316,426; and 5,470,838; the disclosures of which compounds are incorporated herein by reference.

UR precursors and sources thereof include, but are not limited to: prodrugs of UR, such as triphenyluridine, orotic acid and the like; prodrugs of uridine 5'-monophosphate, such as mono- and di-alkyl esters, acyloxyalkyl esters, alkoxycarbonylmethyl esters, substituted ethyl and propyl esters, amidomethyl esters, benzyl esters phenyl esters, phosphonamidates, cyclophosphate esters and the like; UR prodrugs containing mono-, di- or tri-esters of UR, such as mono-, di-, and triacetyl UR and the like; UR prodrugs containing mono, di- or tri-phosphates of UR, such as UR monophosphate, UR diphosphate, UR triphosphate and the like; UR homodimers and their esters, such as U-P-U and the like; heterodimers of dideoxynucleoside compounds and UR or UPase inhibitors, such as AZT-P-U and AZT-P-BAU; etc. Uridine precursors and sources thereof which may be employed in embodiments of the invention include, but are not limited to, those described in U.S. Pat. Nos. 5,723,449 and 7,737,128; the disclosures of which compounds are incorporated herein by reference.

Uridine (UR) Processing Modulators

Where desired, a UR processing modulator may also be administered to the subject in combination with the UPase inhibitor. UR secretion inhibiting compounds include, but are not limited to: drugs, such as dilazep, hexobendine. UR secretion inhibiting compounds which may be employed in embodiments of the invention include, but are not limited to, those described in U.S. Pat. Nos. 6,989,376 and 5,567,689; the disclosures of which compounds are incorporated herein by reference.

UR renal transport competitors include, but are not limited to drugs, such as L-uridine, L-2',3'-dideoxyuridine, D-2',3'-dideoxyuridine. UR renal transport competitors which may be employed in embodiments of the invention include, but are not limited to, those described in U.S. Pat. Nos. 6,989,376; 5,723,449 and 5,567,689; the disclosures of which compounds are incorporated herein by reference.

Formulations

Also provided are pharmaceutical compositions that find use in embodiments of the invention, e.g., that contain a UPase inhibitor and/or UR active agent, e.g., as described above. The active agent(s) may be present in pharmaceutical compositions, e.g., in the form of a pharmaceutically acceptable salt, and can be formulated for oral, topical or parenteral administration for use in the subject methods, as described above. Formulations employed in embodiments of the invention can include a single active agent or a combination of active agents. As such, embodiments of the invention includes formulations that include a single active agent, such as a UPase inhibitor or a UR active agent, as well formulations that include two or more active agents, as where both a UPase inhibitor and a UR active agent are present together in a common formulation.

By way of illustration, UPase inhibitor and, where desired, a UR active agent, (separately or in combination) can be admixed with conventional pharmaceutically acceptable carriers and excipients (e.g., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, eg, U.S. Pat. No. 5,023,252, herein incorporated by reference in its entirety. Such patches may be constructed for continuous, pulsatile, or on demand delivery of pharmaceutical agents.

In certain embodiments of interest, the UPase inhibitor and UR active agent are administered as a single pharmaceutical formulation, that, in addition to the active agent, includes other suitable compounds and carriers, and may also be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents that are well known in the art.

One skilled in the art will appreciate that a variety of suitable methods of administering a formulation of the present invention to a subject or host, eg, patient, in need thereof, are available, and, although more than one route can be used to administer a particular formulation, a particular route can provide a more immediate and more effective reaction than another route. Pharmaceutically acceptable excipients are also well-known to those who are skilled in the art and are readily available. The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Formulations suitable for topical administration may be presented as creams, gels, pastes, or foams, containing, in addition to the active ingredient, and other such carriers that are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to cause a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Optionally, the pharmaceutical composition may contain other pharmaceutically acceptable components, such as buffers, surfactants, antioxidants, viscosity modifying agents, preservatives and the like. Each of these components is well-known in the art. For example, see U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous solution of cyclodextrin also contains dextrose, eg, about 5% dextrose.

Utility

The subject methods find use in the treatment liver diseases. While the target liver disease may vary, in some instances the liver diseases are characterized by the presence of feature fibrosis, or the accumulation of extracellular matrix molecules that make up scar tissue as the toxic endpoint, as well as other diseases such as, inter alia, pulmonary fibrosis, renal fibrosis, systemic sclerosis (SSc), sclerodermatous graft vs. host disease, radiation-induced fibrosis and cardiac fibrosis.

In some instances, the liver disease is a fatty liver disorder. Fatty liver disorders, also known as fatty liver or fatty liver disease (FLD), relates to a condition where large vacuoles of triglyceride fat accumulate in liver cells via the process of steatosis, or abnormal retention of lipids within a cell. Despite having multiple causes, fatty liver is considered a single disease that occurs frequently in subjects with excessive alcohol intake and those who are obese (with or without effects of insulin resistance). The condition is also associated with other diseases that influence fat metabolism. FLD may be categorized into two separate conditions: alcoholic FLD and non-alcoholic FLD. Both conditions show micro-vesicular and macro-vesicular fatty changes at different stages of the disease. Accumulation of fat may also be accompanied by a progressive inflammation of the liver (hepatitis), called steatohepatitis. Fatty liver is also known in the art as alcoholic steatosis and non-alcoholic fatty liver disease (NAFLD), and the more severe forms as alcoholic steatohepatitis (part of alcoholic liver disease) and non-alcoholic steatohepatitis (NASH). Nonalcoholic fatty liver disease-associated cirrhosis is the most severe form of the disease and is characterized by liver inflammation that leads to scarring of the liver tissue, ultimately resulting in liver failure. In some instances, the liver condition is NAFLD, NASH or DILI.

By treatment, is meant that at least an amelioration of the symptoms associated with the condition afflicting the host is achieved, where amelioration is used in a broad sense to refer to at least a reduction in the magnitude of a parameter, e.g., a symptom associated with the condition being treated or a side effect resulting from administration of a drug. As such, treatment also includes situations where the pathological condition, or at least symptoms associated therewith, are completely inhibited, e.g., prevented from happening, or stopped, e.g., terminated, such that the host no longer suffers from the condition, or at least the symptoms that characterize the condition. Treating also include prophylactically treating the subject, such that the liver condition does not occur in the subject. As such, treating includes preventing the occurrence of the liver condition in the subject.

A variety of subjects are treatable according to the subject methods. Generally such hosts are "mammals" or "mammalian," where these terms are used broadly to describe organisms which are within the class mammalia, including the orders carnivore (eg, dogs and cats), rodentia (eg, mice, guinea pigs, and rats), and primates (eg, humans, chimpanzees, and monkeys). In many embodiments, the subjects will be humans.

In certain embodiments, the subjects will be subjects that have been diagnosed for and are, therefore, in need of administration of the active agent. In certain embodiments, the methods may include diagnosing the subject for the presence of the disease condition to be treated by administration of the active agent.

Where the liver disease is DILI, the methods of the invention may be employed in combination with the therapeutic regimen that is suspected to cause the DILI, e.g., to treat DILI that has already occurred or to prophylactically treat DILI. Where the compounds of the invention are administered in conjunction with other therapies, dosages of the co-administered compounds will of course vary depending on the type of co-drug employed, on the specific drug employed, on the condition being treated and so forth. As used herein, the terms "combination treatment", "combination therapy", "combined treatment" or "combinatorial treatment", used interchangeably, refer to a treatment of an individual with at least two different therapeutic agents. The terms "co-administration" or "combined administration" or the like as utilized herein are meant to encompass administration of the selected therapeutic agents to a single patient, and are intended to include treatment regimens in which the agents are not necessarily administered by the same route of administration or at the same time. The term "pharmaceutical combination" means a product that results from the mixing or combining of more than one active ingredient and includes both fixed and non-fixed combinations of the active ingredients. A "fixed combination" means that the active ingredients, e.g. a compound as disclosed herein and one or more additional therapeutic agents, are both administered to a patient simultaneously in the form of a single entity or dosage. A "non-fixed combination" means that the active ingredients, e.g. a compound as disclosed herein and one or more additional therapeutic agents, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients. As used herein, methods of the invention may employed in combination with one or more additional therapeutic agents, such as, without limitation, agents for pulmonary hypertension, such as ambrisentan, bosentan, treprostinil, sildenafil, epoprostenol, treprostinil, iloprost, aldosterone receptor antagonists like spironolactone and eplerenone, angiotensin-converting enzyme inhibitors such as trandolapril, fosinopril, enalapril, captopril, ramipril, moexipril, lisinopril, quinapril, benazepril, and perindopril, angiotensin II inhibitors such as eprosartan, olmesmian, telmismian, losartan, valsmian, candesartan, and irbesmian, anti-anginal agents like nitroglycerin, isosorbide mononitrate, and isosorbide dinitrate, anti-arrhythmic agents including moricizine, quinidine, diisopyramide, phenyloin, propafenone, flecaimide, mexiletine, lidocaine, procainamide, propranolol, acebutolol, amiodarone, dofetilide, dronedarone, sotalol, ibutilide, diltiazem, verapamil, nifedipine, nimodipine, felodipine, nicardipine, clevidipine, isradipine, bepridil, nisoldipine, adenosine, and digoxin, P-adrenergic receptor antagonists like betaxolol, bisoprolol, metoprolol, atenolol, nebivolol, nadolol, carvedilol, labetalol, timolol, carteolol, penbutolol, pindolol, and esmolol, anti-diabetic agents including secretagogues such as sulfonylurea, tolbutamide, acetohexamide, tolazamide, chlorpropamide, glipizide, glyburide, glimepiride, glibenclamide, gliclazide, meglitinide such as nateglinide, senaglinide, repaglinide, insulin sensitizers such as biguanides, metformin, thiazolidinediones such as rosiglitazone, isaglitazone, darglitazone, englitazone, and pioglitazone, a-glucosidase inhibitors such as miglitol, voglibose, emiglitate, and acarbose, glucagon-like peptide analogs and agonists such as exenatide, liraglutide, and taspglutide, dipeptidyl peptidase-4 inhibitors like vildagliptin, sitagliptin, and saxagliptin, amylin analogs such as pramlintide, ligands or agonists of peroxisome proliferator activated receptor (PPAR)-.alpha., .beta., .delta., and .gamma. cholesterol-lowering agents such as hydroxymethylglutaryl-Coenzyme A (HMG-CoA) reductase inhibitors like statins, such as, e.g., atorvastatin, fluvastatin, lovastatin, pitavastatin, pravastatin, rosuvastatin, and simvastatin, agonists of retinoid X receptors (RXR) such as, e.g., ALRT-268, LG-1268, or LG-1069, glucokinase activators, inhibitors of hepatic enzymes involved in stimulation of gluconeogenesis and/or glycogenolysis, diuretics such as acetazolamide, dichlorphenamide, methazolamide, torsemide, furosemide, bumetanide, ethacrynic acid, amiloride, triamterene, indapamide, metolazone, methylclothiazide, hydrochlorothiazide, chlorothiazide, metolazone, bendroflumethiazide, polythiazide, and chlorthalidone, vasodilators like alprostadil, hydralazine, minoxidil, nesiritide, and nitroprusside, and other anti-lipidemic agents like cholestyramine, colestipol, clofibrate, gemfibrozil, probucol or dextrothyroxine.

Kits & Systems

Also provided are kits and systems that find use in practicing the subject methods, eg, as described above. For example, kits and systems for practicing the subject methods may include one or more pharmaceutical formulations, which include the UPase inhibitor and, in some embodiments a UR active agent. As such, in certain embodiments the kits may include a single pharmaceutical composition, present as one or more unit dosages, where the composition includes both UPase inhibitor and a UR active agent. In yet other embodiments, the kits may include two or more separate pharmaceutical compositions, each containing a UPase inhibitor and, optionally, a UR active agent.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, eg, a piece or pieces of paper on which the information is printed, in the packaging of the kit, in a package insert, etc. Yet another means would be a computer readable medium, eg, diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using a plasma UR level modulator, and as a second component (b) a pharmaceutical composition comprising a uridine, an UR prodrug, or an UR mimetic.

Kits of specific interest are those that include a 2, 2'-anhydropyrimidine pharmaceutical composition of the invention and suitable for practicing the subject methods of the invention, such as for mitigating serious liver conditions.

The term "system" as employed herein refers to a collection of a UPase inhibitor, and, optionally a UR active agent present in a single or disparate composition, that are brought together for the purpose of practicing the subject methods. For example, separately obtained UPase inhibitor and UR active agent dosage forms brought together and co-administered to a subject, according to the present invention, are a system according to the present invention.

The following examples further illustrate the present invention but should not be construed in any way as limiting its scope.

EXAMPLES

I. Increase in UR with Increasing Compound I Concentrations.

Because UR is cleared so rapidly, elimination $t_{1/2}$ only a few minutes,[46] and the elimination $t_{1/2}$ of Compound 1 in mice is only 1-2 hours, it is very challenging to measure UR concentrations elevations post discrete doses of Compound I, such as used for ip dosing. For this reason continuous infusion of compound I (authentic TK-112690, Batch TCY90108) to BDF-1 ♂ mice were administered via a sc implanted osmotic pumps and the UR plasma concentration measured.

[46] Deng Y, Wang Z V, Gordillo R, An Y, Zhang C, Liang Q, Yoshino J, Cautivo K M, De Brabander J, Elmquist J K, Horton J D, Hill J A, Klein S, Scherer P E. An adipo-biliary-uridine axis that regulates energy homeostasis. Science 2017, 17; 355(6330)

Solutions of Compound I were prepared at a concentration of 500 mg/mL in sterile PBS. Osmotic pumps (ALZET® micro-osmotic pump 2001D and 1003D, Alza Co) were loaded with 200 µL (2001D osmotic pump) and/or 100 µL (1003D osmotic pump) of TK-112690 solution.

BDF-1 male mice (n=6) were treated with a constant-rate infusion of 667, 833 or 3000 mg/kg/day doses of Compound I delivered via subcutaneously implanted osmotic pumps. Animals were anesthetized with 100 mg/kg ketamine prior to pump implantation. Surgical scissors were used to make an approximately 1 cm incision on the dorsal surface near the shoulder blade of animals. A hemostat was used to carve out a subcutaneous tunnel toward the anterior end of animal. Osmotic pumps were placed inside the subcutaneous tunnel. Incision was sealed with wound clips.

Blood collections were performed on animals anesthetized with ketamine (ip 100 mg/kg). Blood samples from animals treated with a constant-rate infusion of TK-112690 were collected at 72 hours for 667 mg/kg/day and 833 mg/kg/day and 24 hours for 3000 mg/kg/day after pump implantation. Whole blood (~0.8 mL) was drawn through the retro-orbital sinus using a heparin coated micro-hematocrit tube and collected into an EDTA microtainer tube. Blood samples were transferred into fresh 1.5 mL microcentrifuge tubes, and centrifuged for 10 minutes at 14,000×g using an Eppendorf Minispin Plus stored in a 4° C. refrigerator. Exactly 0.4 mL of plasma was transferred into fresh microcentrifuge tubes containing 2 µL of 10 mM 5-FU and vortexed at highest setting for approximately 5 seconds. The final 50 µM concentration of 5-FU served as an internal standard. Animals were sacrificed by cervical dislocation and properly disposed.

Blood samples from animals treated with a constant-rate infusion of compound I were collected at 72 hours for 667 mg/kg/day and 833 mg/kg/day and 24 hours for 3000 mg/kg/day after pump implantation. Whole blood (~0.8 mL) was drawn through the retro-orbital sinus using a heparin coated micro-hematocrit tube and collected into an EDTA microtainer tube. Blood samples were transferred into fresh 1.5 mL microcentrifuge tubes, and centrifuged for 10 minutes at 14,000×g using an Eppendorf Minispin Plus stored in a 4° C. refrigerator. Exactly 0.4 mL of plasma was transferred into fresh microcentrifuge tubes containing 2 µL of 10 mM 5-FU and vortexed at highest setting for approximately 5 seconds. The final 50 µM concentration of 5-FU served as an internal standard. Animals were sacrificed by cervical dislocation and properly disposed.

A solid-phase extraction (SPE) of analytes (UR, Compound I and 5-FU) from plasma was conducted before HPLC analysis. Supelco C8 SPE columns were used for extraction process. All solutions were pushed through SPE columns using positive pressure generated from a Vacuum-Pressure Pump (Barnant Company Model 400-1901). The flow rate through the SPE column was approximately 2 drops per second. Pre-washing of SPE columns was done with a total of 2.4 mL of sterile PBS (room temp; pH=7.4). Exactly 0.6 mL PBS was added to the SPE column four separate times and pushed through the column. Immediately after pre-wash, all 0.4 mL of the plasma sample (with added 5-FU internal standard) was transferred onto the column and pushed through the column. Analytes were disassociated from SPE column by pushing through exactly 0.5 mL of 5 M NaCl (room temp; pH 5). Eluted samples were collected into fresh 1.5 mL micro-centrifuge tubes. Samples were transferred into fresh HPLC vials and analyzed.

HPLC analysis was done at room temperature (RT) using a ThermoFinnigan Spectra System equipped with degasser, pump, autosampler and UV detector. Chromatograms were constructed from a chart recorder equipped with a pen. Analytes were separated using a Phenomenex C18 Reverse-Phase column (250×4.6 mm). Two separate mobile phase gradients were employed for the HPLC analysis: (1) 5% methanol in nano water with 0.1% formic acid (2) 5% methanol in acetonitrile with 0.1% formic acid (flow rate=0.5 mL per minute). HPLC responses for compound I and UR were divided by the 5-FU response. Calibration curves were used to convert these ratios into concentrations of Compound 1.

A regression analysis (UR concentration vs. Compound 1 concentration) for data from the study is provided in FIG. 1. Higher concentrations of Compound 1 are seen to be associated with higher levels of UR.

II. Methionine-Choline Diet (MCD) Model of NASH.

Mice fed an MCD diet is a standard model of diet induced NASH.[47,48] All animals were housed in ventilated standard housing cages throughout the experimental phase. Tap water was provided ad libitum to all animals. Male, 8-week old, C57BL/6 mice from Charles River were acclimated for 3 days maintained on a standard chow diet and group housed in hepa-filtered cages (5 animals per cage) on a normal 12 hours light cycle (at 8 am to 8 pm lights off). The temperature and humidity were 22±2° C. and 50±10%, respectively. Cages litters were changed once a week.

[47] Reid D T, Reyes J L, McDonald B A, Vo T, Reimer R A, Eksteen B. Kupffer Cells Undergo Fundamental Changes during the Development of Experimental NASH and Are Critical in Initiating Liver Damage and Inflammation. PLoS One. 2016, 25; 11:e0159524.

[48] Ramadori P, Weiskirchen R, Trebicka J, Streetz K. Mouse models of metabolic liver injury. Lab Anim. 2015; 49(1 Suppl):47-58.

Following acclimation, the animals were randomized into homogenous treatment groups according to their body weight, and fed ad libitum a diet deficient in methionine and choline: 4.2 kcal/g; MP Biomedicals, Solon, Ohio). Food and water intake were measured 3 times per week (at the same time as body weight measurements). After the acclimation period, the 24 mice (n=6/treatment group) were weighed 3 times per week until sacrifice.

The 4 treatment group were:
Group 1: Vehicle+MCD
Group 2: MCD+200 mg/kg UR
Group 3: MCD+60 mg/kg Compound I
Group 4: MCD+60 mg/kg Compound 1 plus 200 mg/kg UR 30 minutes post Compound 1

All Compound 1 and UR doses (mg/kg in 10 mL/kg of vehicle) were ip, bid at least 8 hours apart, for 28 days. Vehicle=PBS. Vehicle, UR and Compound 1±UR will be dosed daily starting 2 days prior to placing the animals on a MCD diet. Mice were on the MCD diet for 26 days.

After 26 days on MCD, the animals were sacrificed ~2 hours after the last dose and non-fasted glucose was measured along with a plasma lipid panel, TNF-α, ALT and AST. Total body weight was determined weekly. Total liver was weighed and the medial lobe excised, formalin fixed and stained with Oil Red O to evaluate lipid content. An intensity score for the fixed tissue slides measured by an independent histopathologist was also determined.

Figure 2:
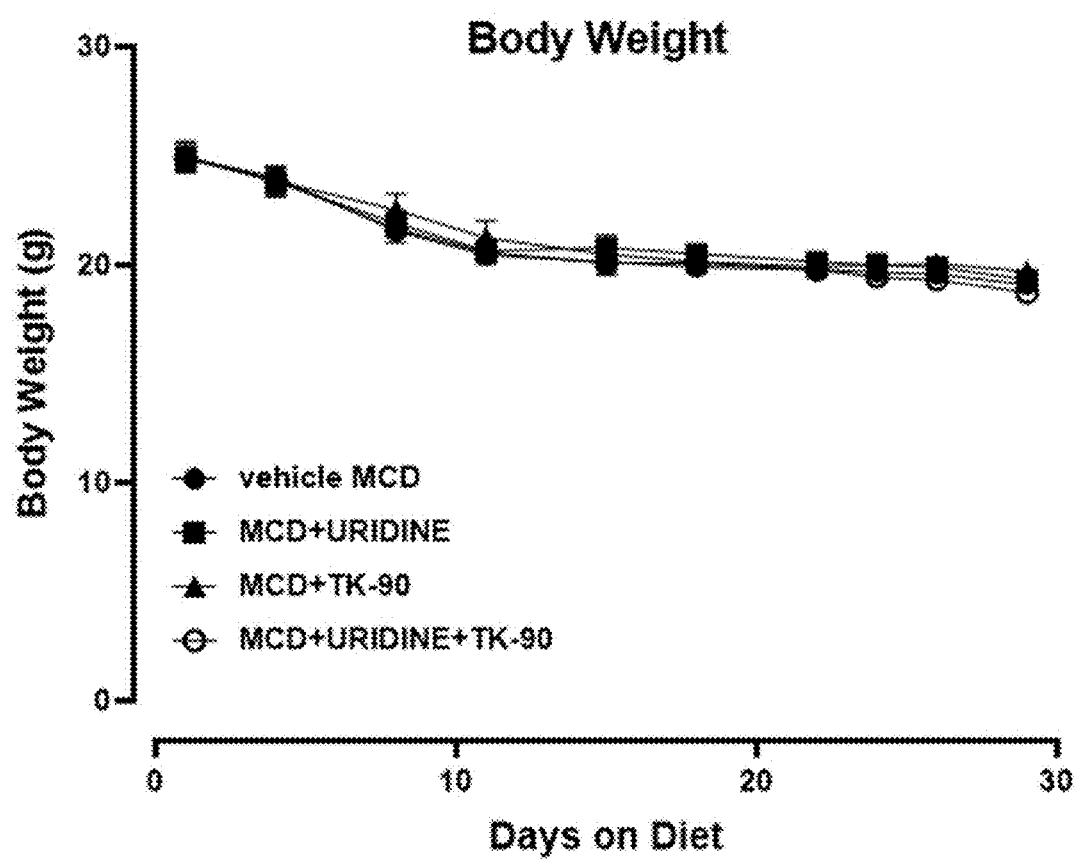
FIG. 2 provides the body weights of the mice measured during the experimental phase of the MCD study. Six mice per experimental group were studied. All groups showed substantial weight loss. No variation in body weight was observed between the groups. Data presented as mean+/−SEM.
Figure 3:
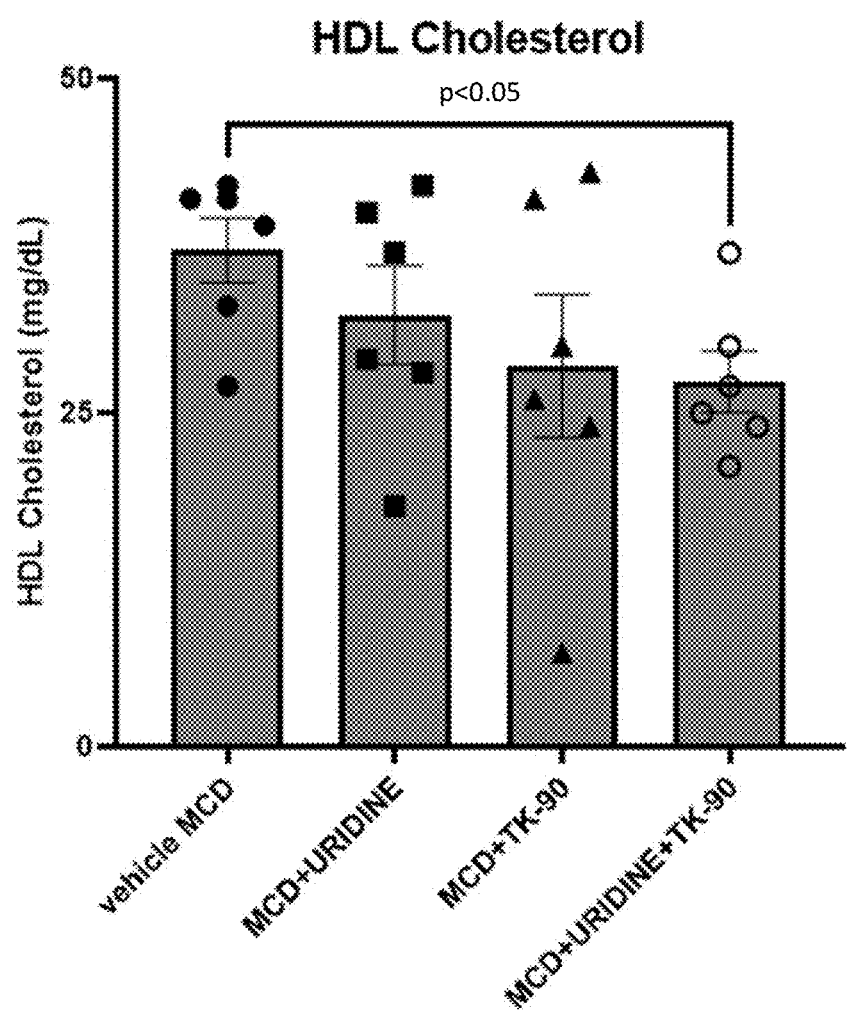
FIG. 3 provides serum HDL cholesterol levels measured at the end of the experimental phase of the MCD study. Six mice per experimental group were studied. Mice treated with UR+Compound 1 (TK-112690) had significantly lower (p<0.05) HDL cholesterol levels compared to vehicle treated controls. Data presented as mean+/−SEM.
Figure 4:
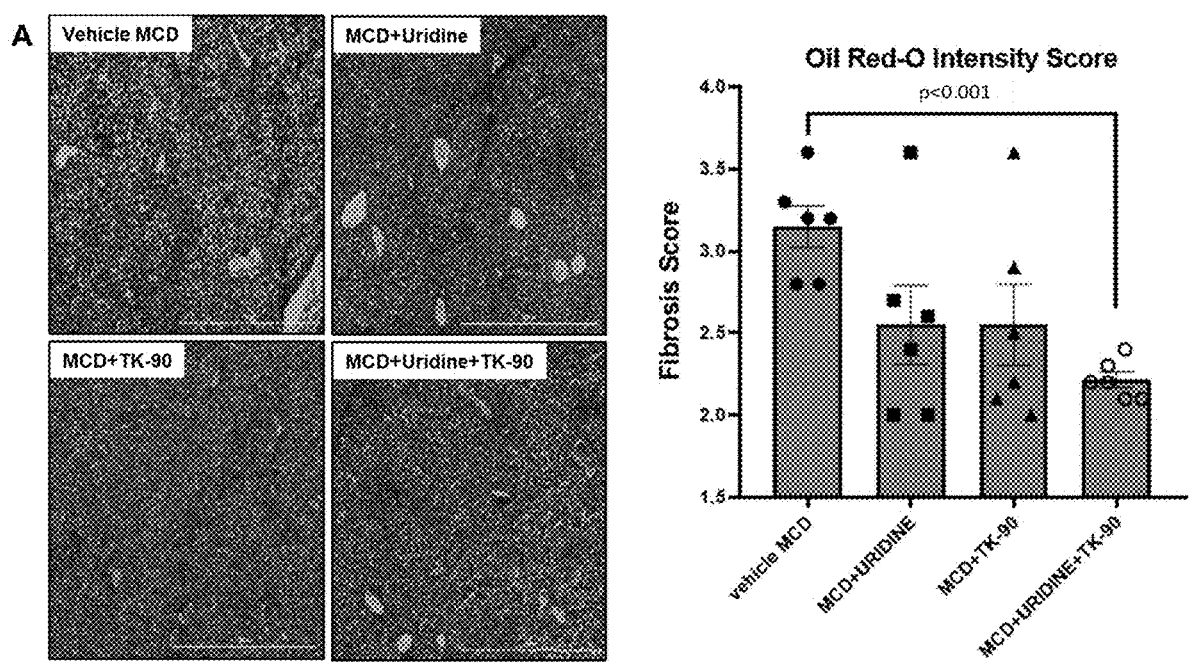
FIG. 4 provides (A) representative H&E images of liver sections from each experimental group and (B) fibrosis scoring of the images shown in (A). The greatest effect was the group of mice treated with UR+Compound 1 (TK-112690). This group displayed significantly (p<0.001) less liver fibrosis compared to vehicle treated controls (six animals per experimental group). Data presented as mean+/−SEM.

As expected,[49] body weight decreased for all treatment groups by approximately 20% (FIG. 2, Data presented as mean+/-SEM.). There was no difference in body weight between groups. There was also no difference with Groups 2, 3, and 4 with respect to total triglycerides, cholesterol, AST or ALT. There was a statistical difference between Group 1 and the group 4 values for HDL-cholesterol (FIG. 3) (Serum HDL cholesterol concentrations measured at the end of the MCD study. Data are means+/-SEM. TK-90 is Compound 1, also known as TK-112690). Most important are the findings for fibrosis (FIG. 4)((A) Representative H&E images of liver sections from each experimental group. (B) Fibrosis scoring of the images shown in (A). TK-90 is Compound 1, also known as TK-112690. Data are means+/-SEM.) The reason for the importance of the data is that fibrosis is the pathologic endpoint for NASH. For the data in FIG. 4, Groups 2, 3, and 4 were all statistically different from the Group 1 control group.

[49] 10. Veteläinen R, van Viet A, van Gulik T M. Essential pathogenic and metabolic differences in steatosis induced by choline or methione-choline deficient diets in a rat model. J Gastroenterol Hepatol. 2007; 22:1526-33.

Notwithstanding the appended claims, the disclosure is also defined by the following clauses:

1. A method of treating a subject for a liver condition, the method comprising:
  administering to the subject an effective amount of a 2,2'-anhydropyrimidine or derivative thereof to treat the subject for the liver condition.

2. The method according to Clause 1, wherein the 2,2'-anhydropyrimidine or derivative thereof is a compound of formula (I):

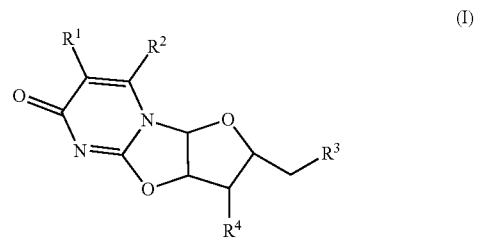

or the pharmaceutically acceptable salts, solvates, hydrates, and prodrug forms thereof, and stereoisomers thereof;
  wherein:
    each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

3. The method according to Clause 2, wherein each $R^1$, $R^2$, $R^3$ and $R^4$ is independently selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

4. The method according to Clause 2, wherein the lower hydrocarbon is selected from the group consisting of alkyl, alkenyl, alkanoyl, aryl, aroyl, aralkyl and alkylamino, and esters thereof.

5. The method according to Clause 2, wherein $R^1$ is hydrogen, fluorine, methyl, ethyl, propyl, benzyl, or 2-bromovinyl; $R^2$ is hydrogen, hydroxyl fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

6. The method according to Clause 5, wherein $R^1$ is hydrogen or methyl; $R^2$ is hydrogen; and each $R^3$ and $R^4$ is independently selected from the group consisting of hydroxyl and benzoyloxy.

7. The method according to Clause 1, wherein the 2,2'-anhydropyrimidine or derivative thereof is selected from the group consisting of: 2,2'-anhydro-5-methyluridine; 3'-O-benzoyl-2,2'-anhydrouridine; 3'-O-benzoyl-2,2'-anhydro-5-methyluridine; 5'-O-benzoyl-2,2'-anhydrouridine; and 5'-O-benzoyl-2,2'-anhydro-5-methyluridine.

8. The method according to Clause 7, wherein the 2,2'-anhydropyrimidine or derivative thereof is 2,2'-anhydro-5-methyluridine.

9. The method according to Clause 7, wherein the 2,2'-anhydropyrimidine or derivative thereof is 3'-O-benzoyl-2,2'-anhydro-5-methyluridine.

10. The method according to Clause 7, wherein the 2,2'-anhydropyrimidine or derivative thereof is 5'-O-benzoyl-2,2'-anhydro-5-methyluridine.

11. The method according to Clause 1, wherein the 2,2'-anhydropyrimidine or derivative thereof comprises a stereoisomer.

12. The method according to Clause 11, wherein the stereoisomer is selected from the group consisting of 2,2'-anhydro-1-(β-D-arabinofuranosyl)-5-methyluracil; 3'-O-benzoyl-2,2'-anhydro-1-(β-D-arabinofuranosyl)-uracil; 3'-O-benzoyl-2,2'-anhydro-1-(β-D-arabinofuranosyl)-5-methyluracil; 5'-O-benzoyl-2,2'-anhydro-1-(β-D-arabinofuranosyl)-uracil; and 5'-O-benzoyl-2,2'-anhydro-1-(β-D-arabinofuranosyl)-5-methyluracil.

13. The method according to any of the preceding clauses, wherein the liver condition is selected from the group consisting of NAFLD, NASH and DILI.

14. The method according to any of the preceding clauses, wherein the treatment is prophylactic.

15. The method according to Clause 14, wherein the liver condition is DILI.

16. The method according to any of Clauses 1 to 13, wherein the subject suffers from the liver condition.

17. A method of treat a subject for a liver condition, the method comprising: administering to the subject an effective amount of a 2,2'-anhydropyrimidine or derivative thereof in combination with a uridine (UR) active agent to treat the subject for the liver condition.

18. The method according to Clause 17, wherein the 2,2'-anhydropyrimidine or derivative thereof is a compound of formula (I):

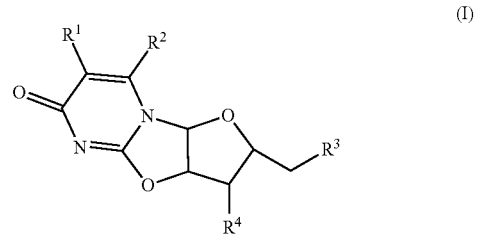

or the pharmaceutically acceptable salts, solvates, hydrates, and prodrug forms thereof, and stereoisomers thereof;
wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

19. The method according to Clause 18, wherein each $R^1$, $R^2$, $R^3$ and $R^4$ is independently selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

20. The method according to Clause 18, wherein the lower hydrocarbon is selected from the group consisting of alkyl, alkenyl, alkanoyl, aryl, aroyl, aralkyl and alkylamino, and esters thereof.

21. The method according to Clause 18, wherein $R^1$ is hydrogen, fluorine, methyl, ethyl, propyl, benzyl, or 2-bromovinyl; $R^2$ is hydrogen, hydroxyl fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

22. The method according to Clause 21, wherein $R^1$ is hydrogen or methyl; $R^2$ is hydrogen; and each $R^3$ and $R^4$ is independently selected from the group consisting of hydroxyl and benzoyloxy.

23. The method according to Clause 18, wherein the 2,2'-anhydropyrimidine or derivative thereof is selected from the group consisting of: 2,2'-anhydro-5-methyluridine; 3'-O-benzoyl-2,2'-anhydrouridine; 3'-O-benzoyl-2,2'-anhydro-5-methyluridine; 5'-O-benzoyl-2,2'-anhydrouridine; and 5'-O-benzoyl-2,2'-anhydro-5-methyluridine.

24. The method according to Clause 23, wherein the 2,2'-anhydropyrimidine or derivative thereof is 2,2'-anhydro-5-methyluridine.

25. The method according to Clause 23, wherein the 2,2'-anhydropyrimidine or derivative thereof is 3'-O-benzoyl-2,2'-anhydro-5-methyluridine.

26. The method according to Clause 23, wherein the 2,2'-anhydropyrimidine or derivative thereof is 5'-O-benzoyl-2,2'-anhydro-5-methyluridine.

27. The method according to Clause 18, wherein the 2,2'-anhydropyrimidine or derivative thereof comprises a stereoisomer.

28. The method according to Clause 27, wherein the stereoisomer is selected from the group consisting of 2,2'-anhydro-1-(β-D-arabinofuranosyl)-5-methyluracil; 3'-O-benzoyl-2,2'-anhydro-1-(β-D-arabinofuranosyl)-uracil; 3'-O-benzoyl-2,2'-anhydro-1-(β-D-arabinofuranosyl)-5- methyluracil; 5'-O-benzoyl-2,2'-anhydro-1-(β-D-arabino-furanosyl)-uracil; and 5'-O-benzoyl-2,2'-anhydro-1-(β-D-arabinofuranosyl)-5-methyluracil.

29. The method according to any of Clauses 17 to 28, wherein the liver condition is selected from the group consisting of NAFLD, NASH and DILI.

30. The method according to any of Clauses 17 to 29, wherein the treatment is prophylactic.

31. The method according to Clause 30, wherein the liver condition is DILI.

32. The method according to any of Clauses 17 to 29, wherein the subject suffers from the liver condition.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a subject for a liver condition selected from the group consisting of NAFLD and NASH, the method comprising:
administering to the subject an effective amount of a 2,2'-anhydropyrimidine or derivative thereof to ameliorate fibrosis to treat the subject for the liver condition, wherein the subject suffers from the liver condition.

2. The method according to claim 1, wherein the 2,2-anhydropyrimidine or derivative thereof is a compound of formula (I):

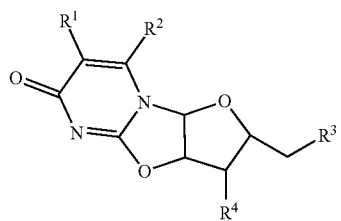

(I)

or the pharmaceutically acceptable salts, solvates, hydrates, and prodrug forms thereof, and stereoisomers thereof;
wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

3. The method according to claim 2, wherein each $R^1$, $R^2$, $R^3$ and $R^4$ is independently selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

4. The method according to claim 2, wherein the lower hydrocarbon is selected from the group consisting of alkyl, alkenyl, alkanoyl, aryl, aroyl, aralkyl and alkylamino, and esters thereof.

5. The method according to claim 2, wherein $R^1$ is hydrogen, fluorine, methyl, ethyl, propyl, benzyl, or 2-bromovinyl; $R^2$ is hydrogen, hydroxyl fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

6. The method according to claim 5, wherein $R^1$ is hydrogen or methyl; $R^2$ is hydrogen; and each $R^3$ and $R^4$ is independently selected from the group consisting of hydroxyl and benzoyloxy.

7. The method according to claim 1, wherein the 2,2'-anhydropyrimidine or derivative thereof is selected from the group consisting of: 2,2'-anhydro-5-methyluridine; 3'-O-benzoyl-2,2'-anhydrouridine; 3*-O-benzoyl-2,2'-anhydro-5-methyluridine; 5'-O-benzoyl-2,2'-anhydrouridine; and 5'-O-benzoyl-2,2'-anhydro-5-methyluridine.

8. The method according to claim 7, wherein the 2,2'-anhydropyrimidine or derivative thereof is 2,2'-anhydro-5-methyluridine.

9. The method according to claim 7, wherein the 2,2'-anhydropyrimidine or derivative thereof is 3'-O-benzoyl-2,2'-anhydro-5-methyluridine.

10. The method according to claim 7, wherein the 2,2'-anhydropyrimidine or derivative thereof is 5'-O-benzoyl-2,2'-anhydro-5-methyluridine.

11. The method according to claim 1, wherein the 2,2'-anhydropyrimidine or derivative thereof comprises a stereoisomer.

12. The method according to claim 11, wherein the stereoisomer is selected from the group consisting of 2,2'-anhydro-1-(β-D-arabinofuranosyl)-5-methyluracil; 3-O-benzoyl-2,2-anhydro-1-(β-D-arabinofuranosyl)-uracil; 3-O-benzoyl-2,2-anhydro-1-(β-D-arabinofuranosyl)-5-methyluracil; 5-O-benzoyl-2,2'-anhydro-1-(β-D-arabinofuranosyl)-uracil; and 5'-O-benzoyl-2,2'-anhydro-1-(β-D-arabinofuranosyl)-5-methyluracil.

13. The method according to claim 1, wherein the liver condition is NASH.

14. The method according to claim 1, wherein the liver condition is NAFLD.

15. A method of treating a subject for a liver condition selected from the group consisting of NAFLD and NASH, the method comprising:
administering to the subject an effective amount of a 2,2'-anhydropyrimidine or derivative thereof in combination with a uridine (UR) active agent to ameliorate fibrosis to treat the subject for the liver condition, wherein the subject suffers from the liver condition.

16. The method according to claim 15, wherein the 2,2'-anhydropyrimidine or derivative thereof is a compound of formula (I):

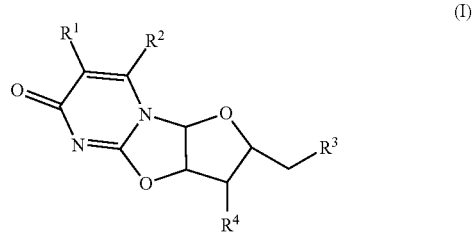

(I)

or the pharmaceutically acceptable salts, solvates, hydrates, and prodrug forms thereof, and stereoisomers thereof;
wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide.

17. The method according to claim 15, wherein the liver condition is NASH.

18. The method according to claim 15, wherein the liver condition is NAFLD.

* * * * *